(12) United States Patent
Yokomizo et al.

(10) Patent No.: US 7,083,972 B2
(45) Date of Patent: Aug. 1, 2006

(54) TRANSFORMANT AND PROCESS FOR PRODUCING POLYESTER BY USING THE SAME

(75) Inventors: Satoru Yokomizo, Kobe (JP); Takeshi Fukuchi, Akashi (JP); Fumio Osakada, Okayama (JP); Keiji Matsumoto, Nishinomiya (JP); Masamichi Takagi, Fuchu (JP); Akinori Ohta, Saitama (JP)

(73) Assignee: Kaneka Corporation, Osaka (JP)

( * ) Notice: Subject to any disclaimer, the term of this patent is extended or adjusted under 35 U.S.C. 154(b) by 414 days.

(21) Appl. No.: 10/019,543

(22) PCT Filed: May 18, 2001

(86) PCT No.: PCT/JP01/04158

§ 371 (c)(1),
(2), (4) Date: Apr. 9, 2002

(87) PCT Pub. No.: WO01/88144

PCT Pub. Date: Nov. 22, 2001

(65) Prior Publication Data

US 2004/0146998 A1    Jul. 29, 2004

(30) Foreign Application Priority Data

May 19, 2000 (JP) .................. 2000-148726
Dec. 27, 2000 (JP) .................. 2000-396955
Jan. 25, 2001 (JP) .................. 2001-016929

(51) Int. Cl.
*C12N 1/15* (2006.01)
*C12N 9/10* (2006.01)
*C12N 9/88* (2006.01)

(52) U.S. Cl. ............... 435/254.2; 435/193; 435/232

(58) Field of Classification Search ........... 435/254.11, 435/254.2, 70.1, 483, 320; 536/23.1, 23; 530/402

See application file for complete search history.

(56) References Cited

U.S. PATENT DOCUMENTS 5,981,257 A * 11/1999 Fukui et al. ................ 435/232

FOREIGN PATENT DOCUMENTS

EP     0 824 148 A2   2/1998
EP     1 352 958 A1   10/2003
JP     10-108682      4/1998

OTHER PUBLICATIONS

Leaf et al. Microbiology. 1996; 142:1169-80.*
Sugiyama et al. Yeast. 1995; 11:43-52.*
Faber et al. Yeast. 1995; 11:1331-1344.*
Masuda et al. Curr. Genet. 1994; 25:412-417.*
Park et al. J. Biol. Chem. 1997; 272(11): 6876-81.*
Yves Poirier, et al., "Synthesis of Polyhydroxyalkanoate in the Peroxisome of *Saccharomyces cerevisiae* by Using Intermediates of Fatty Acid β-Oxidation", *Applied and Environmental Microbiology*, vol. 67, No. 11, pp. 5254-5260 (Nov. 2001).
Timothy A. Leaf, et al., "*Saccharomyces cerevisiae* expressing bacterial polyhydroxybutyrate synthase produces poly-3-hydroxybutyrate", *Microbiology* 142: pp. 1169-1180 (1996).
Toshiaki Fukui, et al., "Co-expression of polyhydroxyalkanoate synthase and (R)-enoyl-CoA hydratase genes of *Aeromonas caviae* establishes copolyester biosynthesis pathway in *Escherichia coli*", *FEMS Microbiology Letters* 170 pp. 69-75 (1999).
T. Fukui, et al., "Cloning and Analysis of the Poly(3-Hydroxybutyrate-*co*-3-Hydroxyhexanoate) Biosynthesis Genes of *Aeromonas caviae*," *J. Bacteriology*, vol. 179, No. 15, Aug. 1997, pp. 4821-4830.
R. Cordero Otero, et al., "Efficient selection of hygromycin-B-resistant *Yarrowia lipolytica* transformants," *Appl. Microbiol. Biotechnol.*, vol. 46, No. 2, 1996, pp. 143-148.

* cited by examiner

*Primary Examiner*—James Ketter
(74) *Attorney, Agent, or Firm*—Kenyon & Kenyon LLP

(57) ABSTRACT

The present invention relates to a gene coding for a copolyester-synthesizing enzyme, a microorganism which utilizes the gene for the fermentative synthesis of a polyester, and a method of producing a polyester with the aid of the microorganism. More particularly, the present invention relates to a gene which functions in a host organism and, by an enzyme, synthesizes a plastic-like polymer degradable under the action of microorganisms in the natural environment (the soil, river or sea). The present invention also, more particularly, relates to a transformant derived from the host organism by transformation with the gene and having an improved ability to fermentatively synthesize a plastic-like polymer, and a method of producing a copolyester with the aid of the transformant.

11 Claims, 11 Drawing Sheets pUTA1 pUAL1 pUAL-ORF2 pUAL-ORF3 pUTA-ORF23

NMR analysis chart

SEQUENCE LISTING

<160> NUMBER OF SEQ ID NOS: 21

<210> SEQ ID NO 1
<211> LENGTH: 1785
<212> TYPE: DNA
<213> ORGANISM: Aeromonas caviae

<400> SEQUENCE: 1

```
atgagccaac catcttatgg cccgctgttc gaggccctgg cccactacaa tgacaagctg      60
ctggccatgg ccaaggccca gacagagcgc accgcccagg cgctgctgca gaccaatctg     120
gacgatctgg gccaggtgct ggagcagggc agccagcaac cctggcagct gatccaggcc     180
cagatgaact ggtggcagga tcagctcaag ctgatgcagc acaccctgct caaaagcgca     240
ggccagccga gcgagccggt gatcacccccg gagcgcagcg atcgccgctt caaggccgag     300
gcctggagcg aacaacccat ctatgactac ctcaagcagt cctacctgct caccgccagg     360
cacctgctgg cctcggtgga tgccctggag ggcgtccccc agaagagccg ggagcggctg     420
cgtttcttca cccgccagta cgtcaacgcc atggccccca gcaacttcct ggccaccaac     480
cccgagctgc tcaagctgac cctggagtcc gacggccaga acctggtgcg cggactggcc     540
ctcttggccg aggatctgga gcgcagcgcc gatcagctca acatccgcct gaccgacgaa     600
tccgccttcg agctcgggcg ggatctggcc ctgaccccgg gccgggtggt gcagcgcacc     660
gagctctatg agctcattca gtacagcccg actaccgaga cggtgggcaa gacacctgtg     720
ctgatagtgc cgcccttcat caacaagtac tacatcatgg acatgcggcc ccagaactcc     780
```

```
ctggtcgcct ggctggtcgc ccagggccag acggtattca tgatctcctg gcgcaacccg    840
ggcgtggccc aggcccaaat cgatctcgac gactacgtgg tggatggcgt catcgccgcc    900
ctggacggcg tggaggcggc caccggcgag cgggaggtgc acggcatcgg ctactgcatc    960
ggcggcaccg ccctgtcgct cgccatgggc tggctggcgg cgcggcgcca gaagcagcgg   1020
gtgcgcaccg ccaccctgtt cactaccctg ctggacttct cccagcccgg ggagcttggc   1080
atcttcatcc acgagcccat catagcggcg ctcgaggcgc aaaatgaggc caagggcatc   1140
atggacgggc gccagctggc ggtctccttc agcctgctgc gggagaacag cctctactgg   1200
aactactaca tcgacagcta cctcaagggt cagagcccgg tggccttcga tctgctgcac   1260
tggaacagcg acagcaccaa tgtggcgggc aagacccaca acagcctgct cgccgtctc    1320 tacctggaga accagctggt gaaggggag ctcaagatcc gcaacacccg catcgatctc    1380
ggcaaggtga agacccctgt gctgctggtg tcggcggtgg acgatcacat cgccctctgg   1440
cagggcacct gcagggcat gaagctgttt ggcggggagc agcgcttcct cctggcggag   1500
tccggccaca tcgccggcat catcaacccg ccggccgcca acaagtacgg cttctggcac   1560
aacggggccg aggccgagag cccggagagc tggctggcag gggcgacgca ccagggcggc   1620
tcctggtggc ccgagatgat gggctttatc cagaaccgtg acgaagggtc agagcccgtc   1680
cccgcgcggg tccggagga agggctggcc cccgccccg gccactatgt caaggtgcgg   1740
ctcaaccccg tgtttgcctg cccaacagag gaggacgccg catga                   1785

<210> SEQ ID NO 2
<211> LENGTH: 405
<212> TYPE: DNA
<213> ORGANISM: Aeromonas caviae

<400> SEQUENCE: 2
atgagcgcac aatccctgga agtaggccag aaggcccgtc tcagcaagcg gttcggggcg     60
gcggaggtag ccgccttcgc cgcgctctcg gaggacttca accccctgca cctggacccg    120
gccttcgccg ccaccacggc gttcgagcgg cccatagtcc acggcatgct gctcgccagc    180
ctcttctccg ggctgctggg ccagcagttg ccgggcaagg ggagcatcta tctgggtcaa    240
agcctcagct tcaagctgcc ggtctttgtc ggggacgagg tgacggccga ggtgaggtg    300 accgccttc gcgaggacaa gcccatcgcc accctgacca ccgcatctt cacccaaggc    360 ggcgccctcg ccgtgacggg ggaagccgtg gtcaagctgc cttaa                   405

<210> SEQ ID NO 3
<211> LENGTH: 1785
<212> TYPE: DNA
<213> ORGANISM: Artificial Sequence
<220> FEATURE:
<223> OTHER INFORMATION: Description of Artificial Sequence: PHA
      synthase gene

<400> SEQUENCE: 3
atgtctcaac catcttatgg tccattgttc gaagctttgg ctcattacaa tgataaattg     60
ttggctatgg ctaaagctca aaccgaaaga actgctcaag ccttgttgca aactaacttg    120
gatgatttgg gtcaagtttt ggaacaaggt tctcaacaac catggcaatt gattcaagct    180
caaatgaatt ggtggcaaga tcaattaaaa ttgatgcaac acactttgtt aaaatctgct    240
ggtcaaccat ctgaaccagt tattactcca gaaagatctg atagaagatt taaagctgaa    300
gcttggtctg aacaaccaat ttatgattac ttaaaacaat cctatttgtt aactgctaga    360
```

-continued

```
catttgttgg cttctgttga tgctttggaa ggtgtcccac aaaaatctag agaaagattg     420
agattcttta ctagacaata cgtcaacgct atggctccat ctaatttctt ggctactaac     480
ccagaattgt taaaattgac tttggaatcc gatggtcaaa atttggttag aggtttggct     540
ttattggctg aagatttgga aagatctgct gatcaattaa acattagatt gactgatgaa     600
tccgcttttg aattaggtag agatttggct ttgactccag gtagagttgt tcaaagaact     660
gaattatatg aattaattca atactctcca actactgaaa ccgttggtaa aaccccagtt     720
ttgatcgttc caccattcat taataaatat tacattatgg atatgagacc acaaaactcc     780
ttggtcgctt ggttggtcgc tcaaggtcaa accgttttca tgatttcctg gagaaaccca     840
ggtgttgctc aagctcaaat tgatttagat gattatgttg ttgatggtgt cattgctgct     900
ttggatggtg ttgaagccgc tactggtgaa agagaagttc acggtattgg ttactgtatt     960
ggtggtaccg ctttgtcttt agctatgggt tggttggccg ccagaagaca aaaacaaaga    1020
gttagaactg ctactttgtt tactactttg ttggatttct cccaaccagg tgaattgggt    1080
atttttattc atgaaccaat tatcgccgcc ttagaagccc aaaatgaagc taaggtatt     1140 atggatggta gacaattggc cgtctccttc tcttttgttga gagaaaactc tttatattgg    1200
aattactata ttgattctta cttaaaaggt caatctccag ttgcttttga tttgttgcac    1260
tggaactctg attctactaa tgttgccggt aaaactcata actctttgtt gagaagatta    1320
tatttggaaa atcaattggt taaaggtgaa ttaaaaatta gaaacactag aattgattta    1380
ggtaaagtta aaactccagt tttgttggtt tctgccgttg atgatcacat tgctttatgg    1440
caaggtacct ggcaaggtat gaaattgttc ggtggtgaac aaagatttt attggccgaa    1500 tccggtcata ttgctggtat tattaatcca ccagctgcta acaaatacgg tttctggcac    1560
aatggtgctg aagctgaatc tccagaatct tggttggctg gtgccaccca tcaaggtggt    1620
tcctggtggc cagaaatgat gggttttatt caaaacagag atgaaggttc tgaaccagtc    1680
ccagccagag tcccagaaga aggtttggct ccagctccag gtcactatgt caaagttaga    1740
ttaaacccag ttttcgcttg tccaaccgaa gaagatgctg cttaa                    1785
```

<210> SEQ ID NO 4
<211> LENGTH: 405
<212> TYPE: DNA
<213> ORGANISM: Artificial Sequence
<220> FEATURE:
<223> OTHER INFORMATION: Description of Artificial Sequence: (R)-
       specific enoyl-CoA hydratase gene

<400> SEQUENCE: 4

```
atgtctgctc aatccttgga agttggtcaa aaagctagat tatctaaaag attcggtgcc      60
gccgaagttg ctgcttttgc tgccttatct gaagatttca acccattgca cttggatcca     120
gcttttgctg ctactaccgc cttcgaaaga ccaatcgtcc atggtatgtt gttagcttct     180
ttattttccg gtttgttggg tcaacaattg ccaggtaaag gttctatttta tttgggtcaa     240 tctttatctt tcaaattgcc agtctttgtc ggtgatgaag ttaccgctga agttgaagtt     300
actgctttga gagaagataa accaattgct actttgacta ctagaatttt cactcaaggt     360
ggtgctttag ctgttaccgg tgaagctgtt gtcaaattgc cataa                      405
```

<210> SEQ ID NO 5
<211> LENGTH: 1036
<212> TYPE: DNA
<213> ORGANISM: Yarrowia lipolytica
<220> FEATURE:

<223> OTHER INFORMATION: promoter ALK3p

<400> SEQUENCE: 5

```
ctgcagcggc gagaccggtt ctgggccgac tacgacgtgc ctggagggac gctccgggag      60
aatctctttg gacgggccaa gatcttcccc gaccaccctg ccggacagta caagtgggaa     120
gaggggagt ttcccttgac caagagtgac aagagtgaga acggcaatgg agtcaatgga      180
gatgagcccg ctactaagaa acaaaaaatc tgaacaagag ccggttttag tacgatacaa     240
gagccggtac gtggacatgc agctgctttt cgaacatgaa gggagcacga ccccacgtat     300
cagtattatg caagggacca gaagtggcct cggcaaaaga ttggcctcgg tcaacaaaag     360
gtcatcatat ccgtctccgc atccgtctgt acgtgaatta tgttacttgt atctttactg     420
tactggtttg gagctacgtc gccaactaat gccaaccagt cctgtggtgt gtctataggt     480
atgtaataca agtacgagta aatgtattgt actggtgcag cacagtagat gacggagacg     540
atgaatcggt caccacccac aaacattgcc tccaaacacc gttatattgt cttactgtcg     600
tggctgagac agactcctcg gggccttgta agaggggaa tgtgtgagac agatgcccac      660
aagtgaccat gcatttttgtg gggcaggaga aaaaccaatg tttgtgggga tagaacccat     720
caaatgaatc taaatgaact ctcccaaaat gaaccactct cttcctccaa tcaaagccct     780
gcgaaatgtc ctccgtctgt ttctcggacc cttagccgta cgacgccata ttacgatagc     840
ccgccacctt aatgcgttta acttgcatgc atgcgtctgc atacagctgc atctgtcata     900
tatgcaccat ttccccacac aactgaagtt tatatatata tactgtaagg actcctgaag     960
tggcacgaac acacctgatc acagcaacat tacagtacac tactctgctc gtattttaca    1020
atactggacg aaaatg                                                    1036
```

<210> SEQ ID NO 6
<211> LENGTH: 1017
<212> TYPE: DNA
<213> ORGANISM: Candida maltosa
<220> FEATURE:
<223> OTHER INFORMATION: promoter ALK1p

<400> SEQUENCE: 6

```
atgcatgaac aggatttaat cccaagaaaa aagtctatttt tctattttca caaggaaact      60
ggaaaaacct ttttgtgttt tgaagtagct ccgtaataac ctgtaaaaaa ataaatttg      120
aagatttgac ttgctgatga aaatgctatc agtgtagctc tagacttgat actagactat     180
gatggcaaca catggtggtc aacgtgcaag acatcaccca atgagaagac tgctaaccag     240
aaaaaaaagg ggacaaaaga aaaactcgag agaaaaagtc aaattggtgt aaaattggct     300
atttttggta cttttcctaat ggggaaatta attgtttaaa attccagttt ttccagagtt    360
aagatttcga ccaattattt ttaatccata tgatcttcat cattatcaac ttgtgaaaaa     420
taataatcga ggtacgttta atacgagata ttagtctacg gctatgaatg ttggatatac     480
ttcattgacg atcagaagct tgattggtta ttcaggtgca tgtgtggata taaacccaac     540
aaattatcta gcaactgtgc cttccccaca ttggtcaaag aaaccctaaa gcaaattaaa     600
atctggataa ataaatcatt catttcacat tttccggtta gtataaggtt ttttaaattt     660
tttttttacag tttagcccctt tcaattacca aatacggtaa caatgtgctt tgtaacatgc    720
agggggattt ctccgttgct gttttctcca catgctttta atgtgtaata aattaaaaaa     780
attacaaaga aaaaccggca tataagcatc ggagtttaca ttgttaacta actgcaaaat     840
ggcgatgttt caaatcaaca aaatttaaaa aaaccccaaa aaaaagtat catataaatt      900
```

```
aaactcaaaa tccttttgat tgcataaaat ttttaaatct cttcttttt ttctttttta      960 ctttcttatc tattctattc ttttttata tatctaattc attttataaca tctggtc       1017

<210> SEQ ID NO 7
<211> LENGTH: 218
<212> TYPE: DNA
<213> ORGANISM: Candida maltosa
<220> FEATURE:
<223> OTHER INFORMATION: terminater ALK1t

<400> SEQUENCE: 7
atagatggat ttttcttttt tatgtgtatt tccggttaat aaatgtttaa attttttttt       60
taataaaaat atttgtagtt atttatatgc aaaaaaaaaa aatattcaaa gcaatcttcc      120
tttctttctt tatctttccc ccatgctaag gtctaaaaca ccacaactta aaacccaact     180
taaccgtata atactaagat caatctccaa agatgcat                              218

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 8
gctctagact gcagcggcga gaccggttct gg                                    32

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 9
ggacacatat gcgtccagta ttgtaaaata cgagc                                 35

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 10
tccccgcggc tgcagcggcg agaccggttc tgg                                   33

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 11
ggacacatat gagccaacca tcttatggcc c                                     31

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Primer
```

```
<400> SEQUENCE: 12
cccagatcgt ccagattggt ctgcag                                          26

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 13
ggacacatat gagcgcacaa tccctggaag t                                    31

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 14
ggggtacctt aaggcagctt gaccacggc                                       29

<210> SEQ ID NO 15
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 15
tttttcagct ggagctcgtc gacatgcatg aacaggattt aatccc                    46

<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 16
ccggaattcc atatgcagat gttataaatg aattagata                            39

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 17
cggaagctta tagatggatt tttcttttt at                                    32

<210> SEQ ID NO 18
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 18
tttttgatat cgagctcgtc gacatgcatc tttggagatt gatctt                    46

<210> SEQ ID NO 19
<211> LENGTH: 5804
```

<212> TYPE: DNA
<213> ORGANISM: Artificial Sequence
<220> FEATURE:
<223> OTHER INFORMATION: Description of Artificial Sequence: Plasmid pSUT5 derived from E. coli/Yarrowia lipolytica

<400> SEQUENCE: 19

| | | | | | |
|---|---|---|---|---|---|
| aggccattct | cgttactgcc | aaaacaccac | ggtaatcggc | cagacaccat | ggacgagtat | 60 |
| ctgtctgact | cgtcattgcc | gcctttggag | tacgactcca | actatgagtg | tgcttggatc | 120 |
| actttgacga | tacattcttc | gttggaggct | gtgggtctga | cagctgcgtt | ttcggcgcgg | 180 |
| ttggccgaca | acaatatcag | ctgcaacgtc | attgctggct | ttcatcatga | tcacattttt | 240 |
| gtcggcaaag | gcgacgccca | gagagccatt | gacgttcttt | ctaatttgga | ccgatagccg | 300 |
| tatagtccag | tctatctata | agttcaacta | actcgtaact | attaccataa | catatacttc | 360 |
| actgccccag | ataaggttcc | gataaaaagt | tctgcagact | aaatttattt | cagtctcctc | 420 |
| ttcaccacca | aaatgccctc | ctacgaagct | cgagctaacg | tccacaagtc | cgcctttgcc | 480 |
| gctcgagtgc | tcaagctcgt | ggcagccaag | aaaaccaacc | tgtgtgcttc | tctggatgtt | 540 |
| accaccacca | aggagctcat | tgagcttgcc | gataaggtcg | gaccttatgt | gtgcatgatc | 600 |
| aagacccata | tcgacatcat | tgacgacttc | acctacgccg | gcactgtgct | cccccctcaag | 660 |
| gaacttgctc | ttaagcacgg | tttcttcctg | ttcgaggaca | gaaagttcgc | agatattggc | 720 |
| aacactgtca | agcaccagta | caagaacggt | gtctaccgaa | tcgccgagtg | gtccgatatc | 780 |
| accaacgccc | acggtgtacc | cggaaccgga | atcattgctg | gcctgcgagc | tggtgccgag | 840 |
| gaaactgtct | ctgaacagaa | gaaggaggac | gtctctgact | acgagaactc | ccagtacaag | 900 |
| gagttcctgg | tcccctctcc | caacgagaag | ctggccagag | gtctgctcat | gctggccgag | 960 |
| ctgtcttgca | agggctctct | ggccactggc | gagtactcca | agcagaccat | tgagcttgcc | 1020 |
| cgatccgacc | ccgagtttgt | ggttggcttc | attgcccaga | accgacctaa | gggcgactct | 1080 |
| gaggactggc | ttattctgac | ccccggggtg | ggtcttgacg | acaagggaga | cgctctcgga | 1140 |
| cagcagtacc | gaactgttga | ggatgtcatg | tctaccggaa | cggatatcat | aattgtcggc | 1200 |
| cgaggtctgt | acgccagaa | ccgagatcct | attgaggagg | ccaagcgata | ccagaaggct | 1260 |
| ggctgggagg | cttaccagaa | gattaactgt | tagaggttag | actatggata | tgtcattaa | 1320 |
| ctgtgtatat | agagagcgtg | caagtatgga | gcgcttgttc | agcttgtatg | atggtcagac | 1380 |
| gacctgtctg | atcgagtatg | tatgatactg | cacaacctgt | gtatccgcat | gatctgtcca | 1440 |
| atggggcatg | ttgttgtgtt | tctcgatacg | gagatgctgg | gtacaagtag | ctaatacgat | 1500 |
| tgaactactt | atacttatat | gaggcttgaa | gaaagctgac | ttgtgtatga | cttattctca | 1560 |
| actacatccc | cagtcacaat | accaccactg | cactaccact | acaccaaaac | catgatcaaa | 1620 |
| ccacccatgg | acttcctgga | ggcagaagaa | cttgttatgg | aaaagctcaa | gagagagaag | 1680 |
| ccaagatact | atcaagacat | gtgtcgcaac | ttcaaggagg | accaagctct | gtacaccgag | 1740 |
| aaacaggcta | gctcgtcgtg | ttcaggaact | gttcgatggt | tcggagagag | tcgccgccca | 1800 |
| gaacatacgc | gcaccgatgt | cagcagacag | ccttattaca | agtatattca | agcaagtata | 1860 |
| tccgtagggt | gcgggtgatt | tggatctaag | gttcgtactc | aacactcacg | agcagcttgc | 1920 |
| ctatgttaca | tcctttttatc | agacataaca | taattggagt | ttacttacac | acggggtgta | 1980 |
| cctgtatgag | caccacctac | aattgtagca | ctggtacttg | tacaaagaat | ttattcgtac | 2040 |
| gaatcacagg | gacggccgcc | ctcaccgaac | cagcgaatac | ctcagcggtc | ccctgcagtg | 2100 |
| actcaacaaa | gcgatatgaa | catcttgcga | tggtatcctg | ctgatagttt | ttactgtaca | 2160 |

-continued

```
aacacctgtg tagctccttc tagcattttt aagttattca cacctcaagg ggagggataa    2220
attaaataaa ttccaaaagc gaagatcgag aaactaaatt aaaattccaa aaacgaagtt    2280
ggaacacaac cccccgaaaa aaaacaacaa acaaaaaacc caacaaaata aacaaaaaca    2340
aaataaatat ataactacca gtatctgact aaaagttcaa atactcgtac ttacaacaaa    2400
tagaaatgag ccggccaaaa ttctgcagaa aaaaatttca aacaagtact ggtataatta    2460
aattaaaaaa cacatcaaag tatcataacg ttagttattt tattttattt aataaaagaa    2520
aacaacaaga tgggctcaaa actttcaact tatacgatac ataccaaata acaatttagt    2580
atttatctaa gtgcttttcg tagataatgg aatacaaatg gatatccaga gtatacacat    2640
ggatagtata cactgacacg acaattctgt atctctttat gttaactact gtgaggcatt    2700
aaatagagct tgatatataa aatgttacat ttcacagtct gaactttttgc agattaccta    2760 atttggtaag atattaatta tgaactgaaa gttgatggca tccctaaatt tgatgaaaga    2820
tgaaattgta aatgaggtgg taaaagagct acagtcgttt tgttttgaga taccatcatc    2880
tctaacgaaa tatctattaa aaatctcagt gtgatcatga gtcattgcca tcctggaaaa    2940
tgtcatcatg gctgatattt ctaactgttt acttgagata aatatatatt tacaagaact    3000
tcccttgaaa ttaatttaga tataaaaatgt ttgcgggcaa gttactacga ggaataaatt    3060
atatctgttg actagaagtt atgaacattc agtatatatg cacatataat aaccaacttc    3120 ggcccctttcg tctcgcgcgt ttcggtgatg acggtgaaaa cctctgacac atgcagctcc    3180
cggagacggt cacagcttgt ctgtaagcgg atgccgggag cagacaagcc cgtcagggcg    3240
cgtcagcggg tgttggcggg tgtcggggct ggcttaacta tgcggcatca gagcagattg    3300
tactgagagt gcaccatacg cgcgctatag ggcgaattgg agctccaccg cggtggcggc    3360
cgctctagaa ctagtggatc ccccgggctg caggaattcg atatcaagct tatcgatacc    3420
gtcgacctcg agggggggcc cggtacccag cttttgtccc tgcgcgctat gcggtgtgaa    3480
ataccgcaca gatgcgtaag gagaaaatac cgcatcaggc gctgcattaa tgaatcggcc    3540
aacgcgcggg gagaggcggt ttgcgtattg ggcgctcttc ctaggcaatt aacagatagt    3600
ttgccggtga taattctctt aacctcccac actcctttga cataacgatt tatgtaacga    3660
aactgaaatt tgaccagata ttgttgtaaa tagaaaatct ggcttgtagg tggcaaaatc    3720
ccgtctttgt tcatcaattc cctctgtgac tactcgtcat cccttttatgt tcgactgtcg    3780 tatttcttat tttccataca tatgcaagtg agatgcccgt gtcctcctcg ctcactgact    3840
cgctgcgctc ggtcgttcgg ctgcggcgag cggtatcagc tcactcaaag gcggtaatac    3900
ggttatccac agaatcaggg gataacgcag gaaagaacat gtgagcaaaa ggccagcaaa    3960
aggccaggaa ccgtaaaaag gccgcgttgc tggcgttttt ccataggctc cgcccccctg    4020
acgagcatca aaaaatcga cgctcaagtc agaggtggcg aaacccgaca ggactataaa    4080
gataccaggc gtttccccct ggaagctccc tcgtgcgctc tcctgttccg accctgccgc    4140
ttaccggata cctgtccgcc tttctccctt cgggaagcgt ggcgctttct caatgctcac    4200
gctgtaggta tctcagttcg gtgtaggtcg ttcgctccaa gctgggctgt gtgcacgaac    4260
cccccgttca gcccgaccgc tgcgccttat ccggtaacta tcgtcttgag tccaacccgg    4320
taagacacga cttatcgcca ctggcagcag ccactggtaa caggattagc agagcgaggt    4380
atgtaggcgg tgctacagag ttcttgaagt ggtggcctaa ctacggctac actagaagga    4440
cagtatttgg tatctgcgct ctgctgaagc cagttacctt cggaaaaaga gttggtagct    4500
```

-continued

```
cttgatccgg caaacaaacc accgctggta gcggtggttt ttttgtttgc aagcagcaga    4560
ttacgcgcag aaaaaaagga tctcaagaag atcctttgat cttttctacg gggtctgacg    4620
ctcagtggaa cgaaaactca cgttaaggga ttttggtcat gagattatca aaaaggatct    4680
tcacctagat cctttaaat taaaaatgaa gttttaaatc aatctaaagt atatatgagt     4740
aaacttggtc tgacagttac caatgcttaa tcagtgaggc acctatctca gcgatctgtc    4800
tatttcgttc atccatagtt gcctgactcc ccgtcgtgta gataactacg atacgggagg    4860
gcttaccatc tggccccagt gctgcaatga taccgcgaga cccacgctca ccggctccag    4920
atttatcagc aataaaccag ccagccgaa gggccgagcg cagaagtggt cctgcaactt     4980
tatccgcctc catccagtct attaattgtt gccgggaagc tagagtaagt agttcgccag    5040
ttaatagttt gcgcaacgtt gttgccattg ctacaggcat cgtggtgtca cgctcgtcgt    5100
ttggtatggc ttcattcagc tccggttccc aacgatcaag gcgagttaca tgatccccca   5160
tgttgtgcaa aaaagcggtt agctccttcg gtcctccgat cgttgtcaga agtaagttgg    5220
ccgcagtgtt atcactcatg gttatggcag cactgcataa ttctcttact gtcatgccat    5280
ccgtaagatg cttttctgtg actggtgagt actcaaccaa gtcattctga aatagtgta    5340 tgcggcgacc gagttgctct tgcccggcgt caatacggga taataccgcg ccacatagca    5400
gaactttaaa agtgctcatc attggaaaac gttcttcggg gcgaaaactc tcaaggatct    5460
taccgctgtt gagatccagt tcgatgtaac ccactcgtgc acccaactga tcttcagcat    5520
cttttacttt caccagcgtt tctgggtgag caaaaacagg aaggcaaaat gccgcaaaaa    5580
agggaataag ggcgacacgg aaatgttgaa tactcatact cttccttttt caatattatt    5640
gaagcattta tcagggttat tgtctcatga gcggatacat atttgaatgt atttagaaaa    5700
ataaacaaat agggggttccg cgcacatttc cccgaaaagt gccacctgac gtctaagaaa    5760
ccattattat catgacatta acctataaaa ataggcgtat cacg                     5804
```

<210> SEQ ID NO 20
<211> LENGTH: 10
<212> TYPE: DNA
<213> ORGANISM: Artificial Sequence
<220> FEATURE:
<223> OTHER INFORMATION: Description of Artificial Sequence: linker DNA

<400> SEQUENCE: 20

```
tactctagag                                                              10
```

<210> SEQ ID NO 21
<211> LENGTH: 1820
<212> TYPE: DNA
<213> ORGANISM: Candida maltosa
<220> FEATURE:
<221> NAME/KEY: misc_feature
<222> LOCATION: (538)..(1413)
<223> OTHER INFORMATION: Ade1

<400> SEQUENCE: 21

```
gatccccttc ttcaaacctt taaatgacat tgtttcgttt ctctatgttt ggtatcggtt     60
cttcttcttc ttcaaaaaaa agggggggcac tattcaaaaa aaatattat aacagtatga    120 tttttttccc tctcccgtcg attgaggttt ttttttttctc tttcgtcttg gtcttttgct   180
tttcactcca aaaatggaaa cacgcgcggc tcaactcgaa atccgtgatc aaaaaaataa    240
aggctgtgag tttcgagcca ataattatga attagtggta ttttttttaa agataaaataa   300 tcaagaatcg cattagggag acgaatatgc gttattcaaa taaaaagaca attctttag    360
```

-continued

```
ggtagcattt cccttcaagt tcatcccaca tgtacattaa tgtcaatgat gtcgcagaag      420
ttaaattagc agaagaaaaa aaaaatgtga attactccga gtcaactctt ctttctcttc      480
ttcttttct tctttatcac cataatcacc accaccacca ccaccaccag ctcccagatg       540
acttcaacta acttagaagg aactttccca ttgattgcca aaggtaaagt cagagatatt     600
taccaagttg acgacaacac tcttttattc gttgctactg atagaatttc cgcatacgat     660
gtgattatgt ctaatggtat cccaaataaa ggtaaaatct taaccaaatt gtctgaattc    720
tggtttgatt tcttgccaat tgaaaaccat ttaatcaaag gagacatttt ccaaaaatat    780
cctcaactag aaccatatag aaaccaattg gaaggcagat ccttacttgt tagaaaattg    840
aaattgatcc ctcttgaagt tattgttaga ggttacatca ccggttccgg ctggaaagaa   900
taccaaaaat ctaaaaccgt ccacggtatt cctattggtg atgtggttga atcacaacaa  960
atcactccta tcttcacccc atccactaaa gcagaacaag gtgaacatga tgaaaatatc  1020
accaaagaac aagctgacaa gattgttgga aaagaattat gtgatagaat tgaaaaaatt  1080
gctattgatt tgtacaccaa agccagagat tacgctgcca ctaaaggaat tattatcgct  1140
gatactaaat ttgaatttgg tttagatggt gacaacatcg ttcttgttga cgaagtttta  1200
actccagatt cttccagatt ctggaatgct gctaaatacg aagttggtaa atctcaagac  1260
tcttacgata aacaattttt gagagattgg ttaacttcta atggtgttgc tggtaaagat  1320
ggtgttgcta tgcctgaaga cattgtcact gaaaccaaga gcaaatacgt tgaagcttac  1380
gaaaatttaa ctggtgacaa atggcaagaa taaattaagg atatctatta ttaaagcttt   1440
ctatttatcc caaactttcg tagtattttc tgacatgttc agatgttttt actttatctt    1500
tcctgaaatt tttgatttct aaccgactct tgcatgtagc tcttgataat gcaacatatg   1560
cttgaccatt agcaaaactt ctacctaaat ctattttgac tctgtccaaa gtttgacctt   1620
gagctttgtg gatcgacatc gcccacgaca agatcatttg gtttgttttt atggtgggtt    1680
attggcactt ggtgcaactg atggtttaac tttggaagag gctaagaaat tgaagacttg    1740
gaatgaagaa cgtgcatctg atttcaaatt gggtgaagaa ttgacttata cttgttataa    1800
aatgtatcat gatgttgatc                                                1820
```

TRANSFORMANT AND PROCESS FOR PRODUCING POLYESTER BY USING THE SAME

TECHNICAL FIELD

The present invention relates to a gene coding for a copolyester-synthesizing enzyme, a microorganism which utilizes said gene for the fermentative synthesis of a polyester, and a method of producing a polyester with the aid of said microorganism. More particularly, the present invention relates to a gene which functions in a host organism and is related to synthesize, by an enzyme, a plastic-like polymer degradable under the action of microorganisms in the natural environment (the soil, river or sea), a transformant derived from said host organism by transformation with said gene and having an improved ability to fermentatively synthesize a plastic-like polymer, and a method of producing a copolyester with the aid of said transformant.

BACKGROUND ART

It is already known that many kinds of microorganisms accumulate polyesters as the energy-storing substance intracellularly. A representative example is a homopolymer of 3-hydroxybutyric acid (hereinafter referred to briefly as 3HB), namely poly-3-hydroxybutyric acid (hereinafter referred to briefly as P(3HB)), which was first discovered in *Bacillus megaterium* in 1925. Since P(3HB) is a thermoplastic polymer biodegradable in the natural environment, it has attracted attention as an eco-friendly plastic. However, because of its high crystallinity, P(3HB) is so hard and brittle that it has found application so far only in a limited assortment of practical uses and much research work has been undertaken to correct for the drawback.

As results of such researches, Japanese Kokai Publication Sho-57-150393 and Japanese Kokai Publication Sho-59-220192 disclose the production technology for a copolymer of 3-hydroxybutyric acid (3HB) and 3-hydroxyvaleric acid (3HV) (hereinafter referred to briefly as P(3HB-co-3HV)). Compared with P(3HB), this P (3HB-co-3HV) is so flexible that it was initially expected to find application in a broader range of end uses. Actually, however, P(3HB-co-3HV) responds poorly to a gain in the molar fraction of 3HV so that particularly the flexibility required of film and the like cannot be improved, thus limiting its scope of use to rigid moldings such as shampoo bottles and throw-away razor handles.

Recently, studies have been undertaken on the binary copolyester of 3HB and 3-hydroxyhexanoic acid (hereinafter referred to briefly as 3HH) (the copolyester will hereinafter be referred to briefly as P(3HB-co-3HH)) and the technology of producing it. For example, such studies have been described in Japanese Kokai Publication Hei-5-93049 and Japanese Kokai Publication Hei-7-265065. The technology described in the above patent literature for the production of P(3HB-co-3HH) comprises fermentative production from a fatty acid, e.g. oleic acid, or an oil or fat, e.g. olive oil, with the aid of a soil-isolated strain of *Aeromonas caviae*. Properties of P(3HB-co-3HH) have also been studied [Y. Doi, S. Kitamura, H. Abe: Macromolecules 28, 4822–4823 (1995)]. In this report referred to above, *Aeromonas caviae* is cultured using a fatty acid of 12 or more carbon atoms as the sole carbon source to fermentatively produce P(3HB-co-3HH) with a 3HH fraction of 11 to 19 mol %. This P(3HB-co-3HH) undergoes a gradual transition from a hard, brittle one to a flexible one with an increasing molar fraction of 3HH and has been found to show flexibility surpassing that of P(3HB-co-3HV). However, this production method is poor in productivity with a cell output of 4 g/L and a polymer content of 30% and, therefore, explorations were made for methods of higher productivity for commercial exploitation.

A PHA (polyhydroxyalkanoic acid)-synthase gene was cloned from a P(3HB-co-3HH)-producible strain of *Aeromonas caviae* [T. Fukui, Y. Doi: J. Bacteriol, Vol. 179, No. 15, 4821–4830 (1997), Japanese Kokai Publication Hei-10-108682]. When this gene was introduced into *Ralstonia eutropha* (formerly, *Alcaligenes eutrophus*) and the production of P(3HB-co-3HH) was carried out using the resulting transformant, the cell output was 4 g/L and the polymer content was 30%. Further, by growing this transformant on vegetable oil as the carbon source, a cell content of 4 g/L with a polymer content of 80% could be accomplished [T. Fukui et al.: Appl. Microbiol. Biotechnol. 49, 333 (1998)]. A process for producing P(3HB-co-3HH) using bacteria, e.g. *Escherichia coli*, or plants as hosts has also been described (WO 00/43525). However, there is no disclosure of the productivity achieved by this production technology.

Since this polymer P(3HB-co-3HH) may have a broadly variable characteristic ranging from a rigid polymer to a flexible polymer depending on the 3HH molar fraction, it can be expected to find application in a broad spectrum of uses from television housings and the like, which require rigidity, to yarn, film and the like which require flexibility. However, the productivity of said polymer is still invariably low in these production methods and none are considered fully satisfactory for practical production methods of this polymer.

Recently, Leaf et al. have conducted studies on the production of biodegradable polyesters using a yeast, which is considered to elaborate acetyl CoA, the precursor of 3HB, with good efficiency as a producer organism (Microbiology, Vol. 142, pp 1169–1180 (1996)). They introduced the *Ralstonia eutropha* polyester synthase gene into *Saccharomyces cerevisiae*, a kind of yeast, to construct a transformant and cultured it using glucose as the carbon source, to thereby confirm the accumulation of P(3HB) (polymer content 0.5%). However, the polymer produced in this study was P (3HB), which is hard and brittle.

It is known that yeasts are fast-growing, with high cell productivity. The yeast cell attracted attention as the single cell protein in the past and studies on the production of yeast cells for use as a feedstuff using n-paraffin as the carbon source, while their component nucleic acids have been utilized as seasonings. Furthermore, since yeasts are considered to produce acetyl-CoA, which is a precursor of the polymer, with high efficiency, a high polymer productivity is expected. Moreover, since the separation of cells from the culture broth is easy as compared with bacteria, it is possible to simplify the polymer extraction and purification process. Therefore, a demand has existed for a process for producing P(3HB-co-3HH) having beneficial physical properties with the aid of yeasts.

DISCLOSURE OF INVENTION

In light of the above state of the art, the present invention has for its object to provide a polyester synthesis-associated gene which functions and can be expressed with good efficiency in a yeast, a transformant of the yeast as transformed with a gene expression cassette comprising said gene, and a method of producing a polyester which is biodegradable and has excellent physical properties, such as P(3HB-co-3HH), which comprises growing the transformant obtained.

After many investigations, the inventors of the present invention constructed a gene expression cassette by ligating a promoter and a terminator, both of which substantially function in a yeast, to at least one enzyme gene related to the synthesis of a copolyester through copolymerization of 3-hydroxyalkanoic acids of the following general formula (1) and can be substantially expressed in the yeast, introduced said gene expression cassette into a yeast to construct a transformant, and cultured said transformant, whereby a polyester, which is a copolymer of 3-hydroxyalkanoic acids of the following general formula (1), could be successfully harvested from the resulting culture.

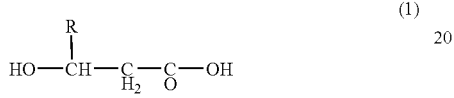

(1)

in the formula, R represents an alkyl group.

The present invention, therefore, is concerned with a transformant wherein at least one kind of gene expression cassettes comprising a polyester synthesis-associated enzyme gene has been introduced into a yeast.

The present invention is further concerned with a method of producing a polyester using said transformant which comprises growing said transformant and harvesting the polyester from the resulting culture.

The term "substantially" as used herein means that referring to the sequence of the polyester synthesis-associated gene and the gene sequences such as a promoter and terminator, among others, which are necessary for the construction of the gene expression cassette, the nucleotide sequences may have undergone mutation, such as deletion, substitution and/or insertion, as far as the functions of the gene and the functions necessary for gene expression are retained.

Furthermore, the present invention is related to a polyester synthesis-associated enzyme gene which is modified from at least one gene code CTG to TTA, TTG, CTT, CTC or CTA.

The present invention is now described in detail.

Figure 1:
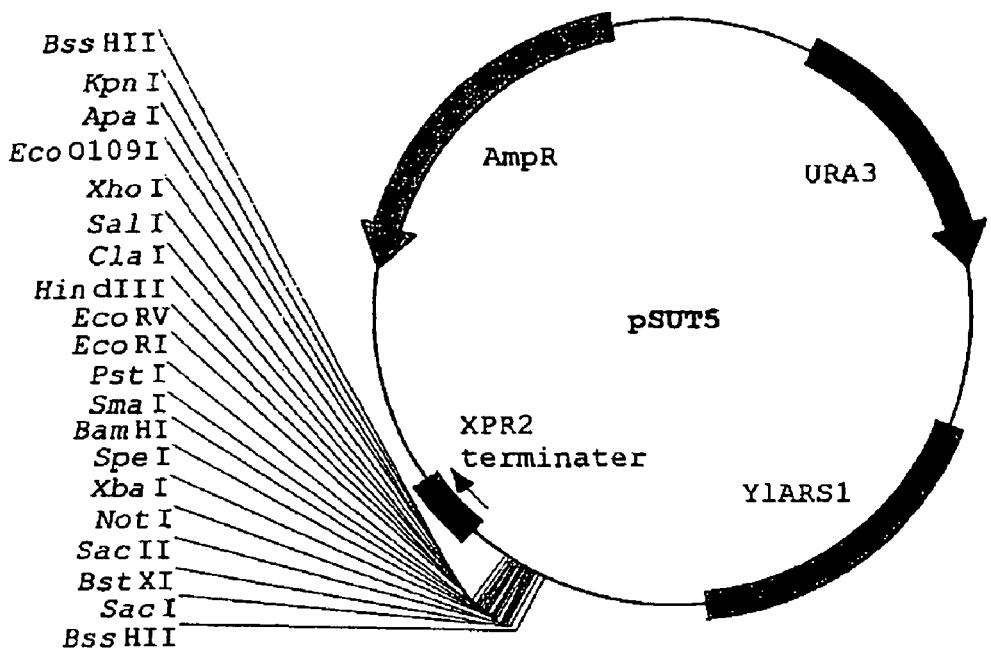
FIG. 1 is a schematic diagram showing the plasmid pSUT5 used as a vector in Example 2 (a).

BEST MODE FOR CARRYING OUT THE INVENTION (1) The Host

The yeast to be used is not particularly restricted but may be any of the yeasts belonging to the following genera and deposited with any of authoritative culture collections (such as IFO, ATCC, etc.):

*Aciculoconidium, Ambrosiozyma, Arthroascus, Arxiozyma, Ashbya, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkara, Dipodascopsis, Dipodascus, Eeniella, Endomycopsella, Eremascus, Eremothecium, Erythrobasidium, Fellomyces, Filobasidium, Galactomyces, Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtzmanomyces, Leucosporidium, Lipomyces, Lodderomyces, Malassezia, Metschnikowia, Mrakia, Myxozyma, Nadsonia, Nakazawaea, Nematospora, Ogataea, Oosporidium, Pachysolen, Phachytichospora, Phaffia, Pichia, Rhodosporidium, Rhodotorula, Saccharomyces, Saccharomycodes, Saccharomycopsis, Saitoella, Sakaguchia, Saturnospora, Schizoblastosporion, Schizosaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichosporiella, Trichosporon, Trigonopsis, Tsuchiyaea, Udeniomyces, Waltomyces, Wickerhamia, Wickerhamiella, Williopsis, Yamadazyma, Yarrowia, Zygoascus, Zygosaccharomyces, Zygowilliopsis, Zygozyma.*

As the yeast used for the transformant according to the present invention, *Candida malosa* or *Yarrowia lipolytica* is preferred and *Candida malosa* is particularly preferred.

(2) The Polyester Synthesis-associated Enzyme Gene

The polyester synthesis-associated enzyme gene is not particularly restricted but is preferably one coding for an enzyme derived from a bacterium. Specifically, preferred is an enzyme gene associated with the synthesis of a copolyester of 3-hydroxyalkanoic acids of the above general formula (1), more preferred is an enzyme gene associated with the synthesis of P(3HB-co-3HH) which is a copolyester resulting from the copolymerization of 3-hydroxybutyric acid of the following formula (2) and 3-hydroxyhexanoic acid of the following formula (3).

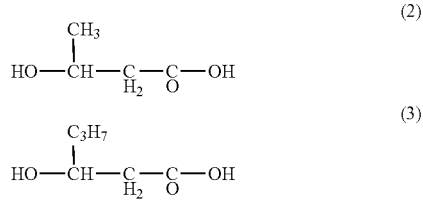

The enzyme gene involved in the synthesis of a copolyester of 3-hydroxyalkanoic acids of the above general formula (1) is not particularly restricted but may for example be the polyester synthase gene described in Japanese Kokai Publication Hei-10-108682. As a specific example of such polyester synthase gene, a PHA synthase gene can be mentioned. Furthermore, a polyester synthesis-associated enzyme gene may be used in combination with the present polyester synthase genes. Such enzyme genes include (R)-specific enoyl-CoA hydratase gene which converts enoyl-CoA, an intermediate in the β-oxidation pathway, to thereby synthesize monomeric (R)-3-hydroxyacyl-CoA [T. Fukui et al.: FEMS Microbiology Letters, Vol. 170, 69–75 (1999)], β-ketothiolase gene which dimerizes acetyl-CoA to monomeric 3-hydroxybutyryl-CoA, and NADPH-dependent acetoacetyl-CoA reductase gene [Peoples O P et al.: J. Biol. Chem., 264 (26) 15298–15303 (1989)].

Some species of said host yeast show abnormalities in the translating of genetic codes. For example, *Candida cylindracea* [Y. Kawaguchi et al., Nature 341, 164–166 (1989)] and *Candida maltosa* [H. Sugiyama et al., Yeast 11, 43–52 (1995)] are nonconventional yeasts in which the genetic code CTG is not translated into leucine but into serine. When a polyester synthesis-associated enzyme gene is to be expressed in such a yeast, genetic code translating abnormalities may take place so that an enzyme having an amino acid sequence different from that of the proper enzyme is produced at times. Therefore, the function of this enzyme is not fully exhibited.

Such a phenomenon can be avoided by using a gene constructed by modifying the genetic code CTG contained in the gene beforehand to a different genetic code corresponding to leucine (TTA, TTG, CTT, CTC, CTA).

Analysis of the genetic codes of organisms inclusive of yeasts reveals that the frequency of usage of genetic codes varies widely with different organisms. Thus, among a plurality of genetic codes specifying the same amino acid, the genetic code to be used vary with different organisms and it has been pointed out that the translation efficiency of a gene consisting of genetic codes with high frequencies of use is high. For example, the GC contents of *Aeromonas caviae* PHA synthase gene and (R)-specific enoyl-CoA hydratase gene are 67.16% and 65.77%, respectively, but among the enzymes so far reported in *Candida maltosa*, the contents are 39.55% for phosphoglycerate kinase and 35.67% for ALK2-A. Therefore, in order that a polyester synthesis-associated gene may be efficiently expressed in *Candida maltosa*, for instance, it is preferable to use said gene in which said genetic code CTG is changed to a different genetic code specifying leucine and, at the same time, the genetic codes are changed to those with high frequency of use.

The polyester synthesis-associated enzyme gene of the invention may be used as it is in a yeast which shows no translating abnormality of the genetic codes. As an alternative, a modified gene as modified by changing genetic codes to those used by the particular yeast with high frequencies without alternation of the amino acid sequence may be used. In a yeast which shows translating abnormality of genetic codes, the CTG codon of said enzyme gene may be changed to TTA, TTG, CTT, CTC or CTA, or a gene as modified by changing genetic codes to those used by the particular yeast with high frequencies without alternation of the amino acid sequence may be used. For example, when the host is *Candida maltosa*, the gene identified in SEQ ID NO:3 or NO:4 can be used as the polyester synthesis-associated enzyme gene of the invention. The nucleotide sequence of this gene may have undergone mutation, such as deletion, substitution, insertion and/or the like, provided that the resulting mutant gene produces the said polyester synthesis-associated enzyme.

The polyester synthesized by said PHA synthase is a copolymer of 3-hydroxyalkanoic acids of the above general formula (1), and can be represented by the general formula (4) shown below. Preferred is the copolyester P(3HB-co-3HH) obtainable by copolymerization of 3-hydroxybutyric acid of the above formula (2) and 3-hydroxyhexanoic acid of the above formula (3) and can be represented by the following general formula (5).

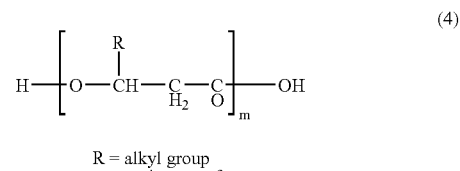

R = alkyl group
m = an integer of not less than 2

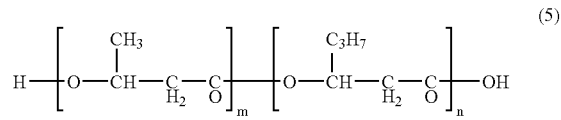

m, n = an integer of not less than 1

(3) Construction of a Gene Expression Cassette

For the expression of a gene in a yeast, it is necessary to ligate DNA sequences such as a promoter, UAS, etc. upstream of the 5'-end of the gene and to ligate DNA sequences such as poly-A addition signal, terminator, etc. downstream of the 3'-end of the gene. These DNA sequences maybe any arbitrary sequences that may function in the yeast. While the promoter includes sequences relevant to constitutive expression and sequences relevant to inducible expression, whichever kind of such promoter sequence can be employed.

Moreover, in the transformant of the invention, the above promoter and terminator are preferably those which function in the organism used for the production of a polyester.

Construction of a gene expression cassette to be used for the construction of a transformant according to the invention is now described, referring to (a) the case in which *Yarrowia lipolytica* is used as the host and (b) the case in which *Candida maltosa* is used as the host as examples.

(a) When *Yarrowia lipolytica* is Used as the Host

When *Yarrowia lipolytica* is used as the host, the promoter and terminator to be used are preferably those derived from *Yarrowia lipolytica*. More preferably, a promoter derived from *Yarrowia lipolytica* ALK3 and a terminator derived from *Yarrowia lipolytica* XRP2 are used. The DNA sequence of said promoter and/or terminator may be the DNA sequence derived by the deletion, substitution and/or addition of one or more nucleotides as far as it may function in *Yarrowia lipolytica*.

The vector for use in the above construction may be any vector which is a plasmid capable of autonomous replication in *Escherichia coli* and may have a region which will be autonomously replicated in the yeast. Such a vector capable of autonomous replication in the yeast will be contained intracellularly. Moreover, the gene expression cassette can then be integrated onto the chromosome. In *Yarrowia lipolytica*, the autonomously replicating pSAT4 and pSUT5 can be employed (Toshiya Iida: Studies on the n-alkane-inductive cytochrome P450 gene group of the yeast *Yarrowia lipolytica*, a doctorate dissertation thesis, Tokyo University Graduate School, 1997).

In the above yeast, the polyester synthesis-associated enzyme gene is preferably a gene derived from *Aeromonas caviae*, and for example, the *A. caviae*-derived PHA synthase gene (hereinafter referred to briefly as phaC) (SEQ ID NO:1) or the (R)-specific enoyl-CoA hydratase gene (hereinafter referred to briefly as phaJ) which converts phaC and enoyl-CoA, which is an intermediate in the β-oxidation pathway, to the monomeric (R)-3-hydroxyacyl-CoA [T. Fukui et al., FEMS Microbiology Letters, Vol. 170, 69–75 (1999)] (SEQ ID NO:2) can be used with advantage.

The promoter ALK3p (SEQ ID NO:5) (GenBank AB010390) of *Yarrowia lipolytica* Alk3 gene can be ligated upstream of the 5'-end of each of these structural genes.

To prepare the restriction enzyme site necessary for linking the promoter to the structural gene, a PCR technique can be utilized. The primer sequences used in the PCR are shown in SEQ ID NO:8 through NO:14. PCR conditions may be arbitrary as far as the objective gene fragment can be amplified.

Figure 3:
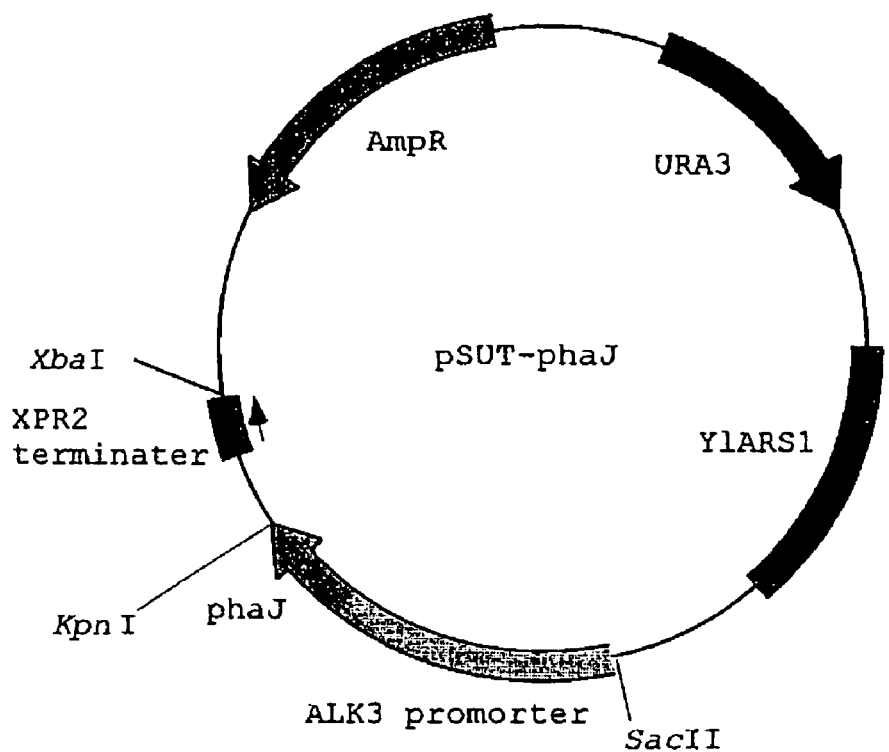
FIG. 3 is a schematic diagram showing the plasmid pSUT-phaJ constructed in Example 2 (a).
Figure 4:
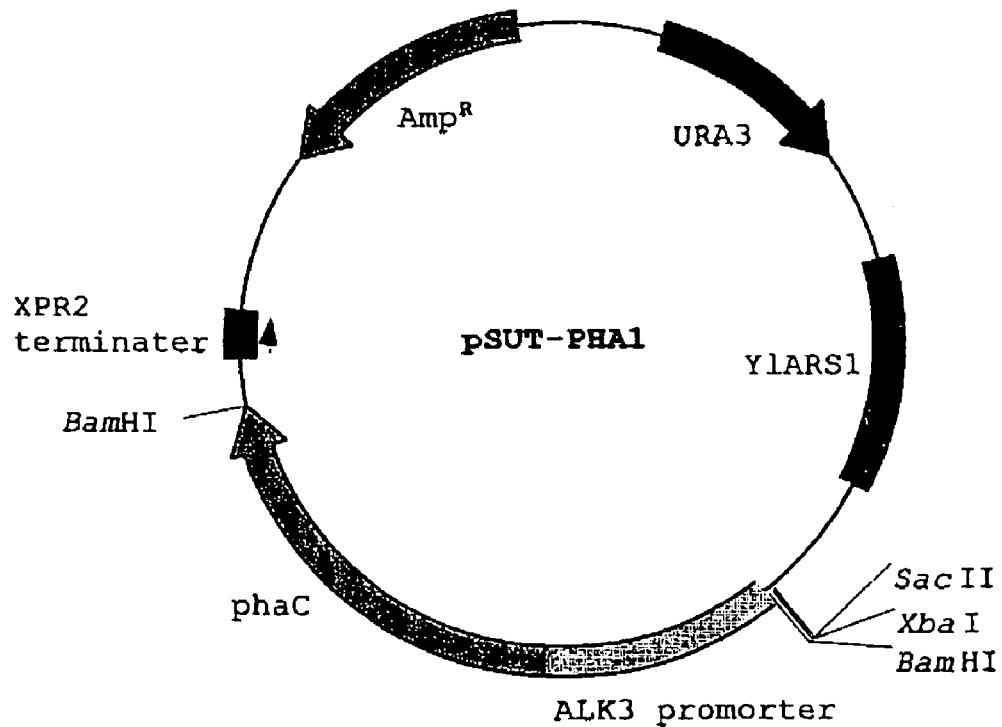
FIG. 4 is a schematic diagram showing the plasmid pSUT-PHA1 constructed in Example 2 (a).

As to the promoter, ALK3X with XbaI at 5'-end and NdeI at 3'-end and ALK3S with SacII at 5'-end and NdeI at 3'-end can be constructed from SEQ ID NO:8 and NO:9 and SEQ ID NO:9 and NO:10, respectively, using SEQ ID NO:5 as a template. As to phac, a 100-bp (approx.) fragment with NdeI at 5'-end and PstI at 3'-end can be constructed from SEQ ID NO:11 and NO:12 using SEQ ID NO:1 as a template. To this fragment is ligated the remaining 1700-bp (approx.) PstI-BamHI fragment to construct the full-length phaC with NdeI at 5'-end and BamHI at 3'-end. As to phaJ, phaJ fragment with NdeI at 5'-end and KpnI at 3'-end can be constructed from SEQ ID NO:13 and NO:14 using SEQ ID NO:2 as a template. As to the vector, the plasmid vector pSUT5 (FIG. 1, SEQ ID NO:19) and the vector pSUT6 obtainable by changing the NdeI site of pSUT5 to an XbaI site by using a linker DNA shown in SEQ ID NO:20 can be used. To the multi-cloning site SacII, KpnI of pSUT6, ALK3S and phaJ can be ligated to construct a plasmid pSUT-phaJ (FIG. 3). Then, to the multi-cloning site XbaI, BamHI of pSUT5, ALK3X and phaC can be ligated to construct a plasmid pSUT-PHA1 (FIG. 4).

Figure 5:
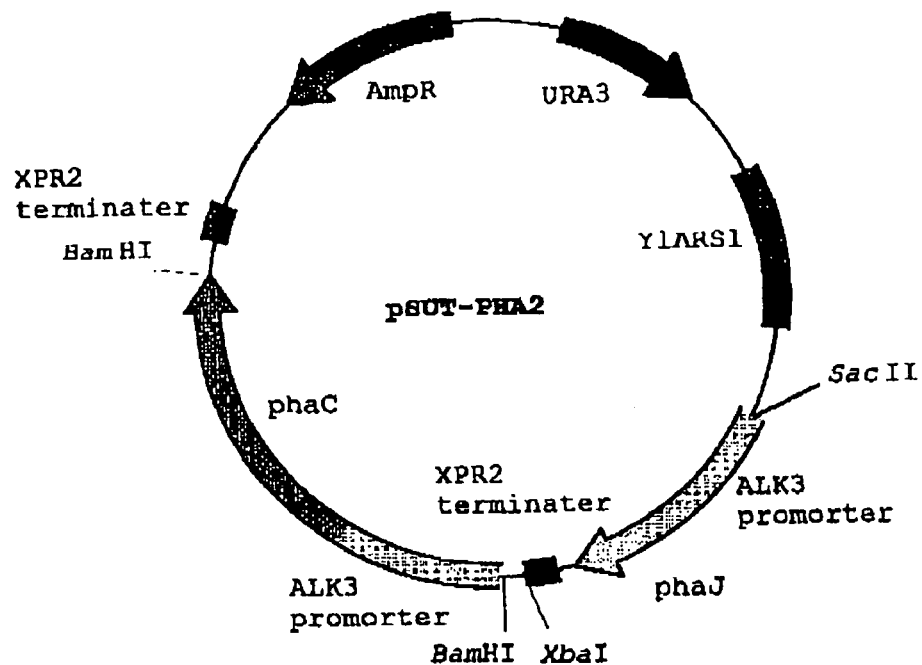
FIG. 5 is a schematic diagram showing the plasmid pSUT-PHA2 constructed in Example 2 (a).

Further, ALK3S, phaJ and downstream terminator can be excised as a unit from the plasmid pSUT-phaJ using SacII and XbaI and ligated to the SacII, XbaI site of plasmid pSUT-PHA1 to construct a plasmid pSUT-PHA2 (FIG. 5). In this manner, two kinds of plasmids for recombination can be constructed.

By the above procedure, there can be constructed a gene expression cassette for the production of a copolyester of 3-hydroxyalkanoic acids of the above general formula (1) in the yeast *Yarrowia lipolytica*.

(b) When *Candida maltosa* is Used as the Host

When *Candida maltosa* is used as the host, the promoter and terminator to be used are preferably those which function in *Candida maltosa*, more preferably those derived from *Candida maltosa*. Still more preferably, the promoter and terminator derived from *Candida maltosa* ALK1 are used. The DNA sequence of said promoter and/or terminator may be a DNA sequence derived by the deletion, substitution and/or addition of one or more bases only provided that the sequence may function in *Candida maltosa*.

The vector for use in the construction may be the same as the one referred to above for the case (a). In *Candida maltosa*, the autonomously replicating pUTU1 can be used [M. Ohkuma at al., J. Biol. Chem., Vol. 273, 3948–3953 (1998)].

When *Candida maltosa* is used as the host, the polyester synthesis-associated enzyme gene is preferably the gene coding for the same amino acid sequence as the *Aeromonas caviae*-derived enzyme. For example, the gene coding for the same amino acid sequence as the *Aeromonas caviae*-derived PHA synthase in *Candida maltosa* (this gene is hereinafter referred to briefly as ORF2, which is defined by SEQ ID NO:3), or the gene coding for the same amino acid sequence, in *Candida maltosa*, as ORF2 and the (R)-specific enoyl-CoA hydratase which converts enoyl-CoA, which is an intermediate in the β-oxidation pathway, to the monomeric (R)-3-hydroxyacyl-CoA (this gene is hereinafter referred to briefly as ORF3, which is defined by SEQ ID NO:4) [T. Fukui et al., FEMS Microbiology Letters, Vol. 170, 69–75 (1999)], can be used with advantage.

The promoter ALK1p (SEQ ID NO:6) and terminator ALK1t (SEQ ID NO:7) (GenBank D00481) [M. Takagi et al., Agric. Biol. Chem., Vol. 5, 2217–2226 (1989)] of the *Candida maltosa* Alk1 gene can be ligated upstream of the 5'-end and downstream of the 3'-end respectively in each of these structural genes.

To prepare the restriction enzyme site for linking the promoter and terminator to the structural gene, a PCR technique can be utilized. The primer sequences for use in the PCR are shown in SEQ ID NO:15 through NO:18. The conditions mentioned above for the case (a) can be employed as the consitions for the PCR.

Figure 2:
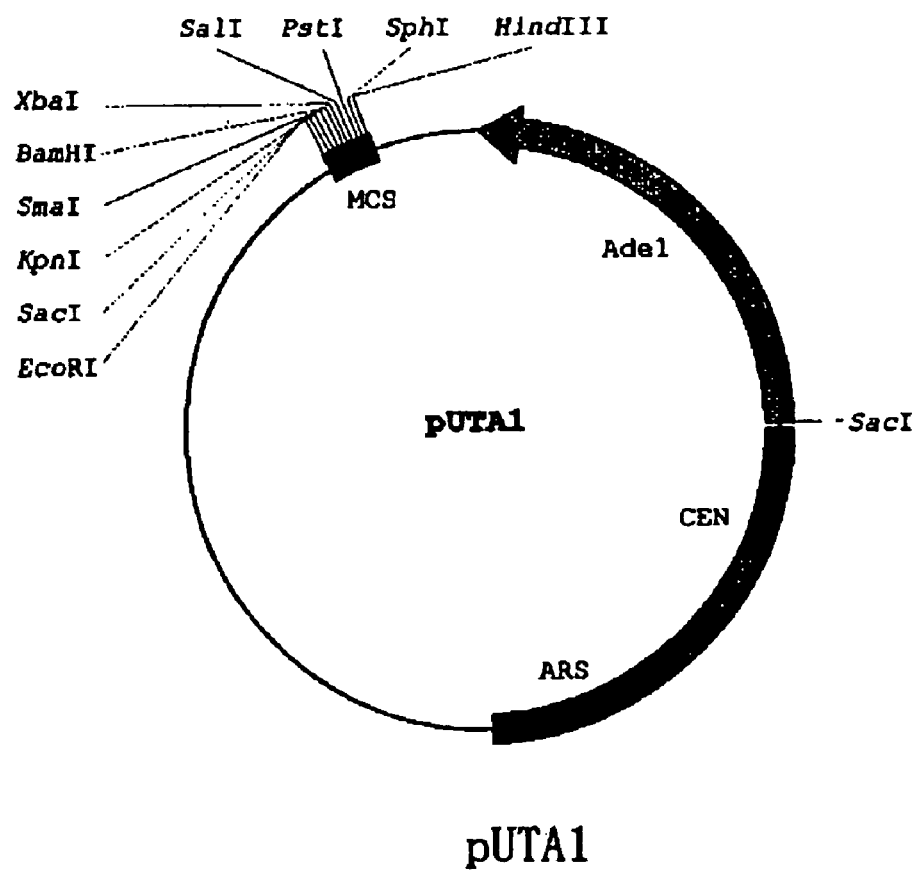
FIG. 2 is a schematic diagram showing the plasmid pUTA1 used as a vector in Example 2 (b).

As to the promoter region, ALK1p with PvuII at 5'-end and EcoRI at 3'-end can be prepared from SEQ ID NO:15 and NO:16 using SEQ ID NO:6 as a template. As to the terminator region, ALK1t with HindIII at 5'-end and EcoRV at 3'-end can be prepared from SEQ ID NO:17 and NO:18 using SEQ ID NO:7 as template. As to the vector, the vector pUTA1 (FIG. 2) prepared by modifying the marker gene from Ura3 to Ade1 using pUTU1 and *Candida maltosa* Ade1 gene (SEQ ID NO:21, GenBank D00855) [S. Kawai et al., Agric. Biol. Chem., Vol. 55, 59–65 (1991)]. By ligating ALK1p to the PvuII, EcoRI site of pUCNT (described in WO 94/03613) and ALK1t to the HindIII, SspI site of the pUCNT, pUAL1 (FIG. 6) can be constructed. Then, by ligating ORF2 to the NdeI, PstI site of pUAL1, the plasmid pUAL-ORF2 (FIG. 7) can be constructed. Further, by ligating ORF3 to the NdeI, HindIII site of pUCNT-ALK1t in the course of construction of pUAL1 and further ligating ALK1p, pUAL-ORF3 (FIG. 8) can be constructed.

Then, by excising ORF2, upstream promoter and downstream terminator as a unit from the plasmid pUAL-ORF2 using EcoT22I and ligating it to the PstI site of pUTA1, pUTA-ORF2 can be constructed.

In addition, by excising ORF3, upstream promoter and downstream terminator as a unit from pUAL-ORF3 using SalI and ligating it to the SalI site of pUTA-ORF2, a plasmid pUTA-ORF23 (FIG. 9) can be constructed.

By the above procedure, there can be constructed a gene expression cassette for the production of a copolyester of alkanoic acids of the above-general formula (1) in the yeast *Candida maltosa*.

(4) Construction of a Transformant

Introduction of the polymer synthesis-associated gene expression cassette cloning vector into a yeast can be carried out by the per se known method. Thus, the calcium method [Lederberg. E. M. et al., J. Bacteriol, 119, 1072 (1974)] or the electroporation method [Current Protocols in Molecular Biology, 1, 1. 8. 4., 1994], for instance, can be employed. A commercial transformation kit, such as Fast Track™-Yeast Transformation Kit$^{SM}$ (Geno Technology), can also be utilized.

For example, *Yarrowia lipolytica* CXAU1 strain [T. Iida et al., Yeast, 14, 1387–1397 (1998)] can be used as the host. By transforming this strain with the polymer synthesis-associated gene expression cassette by the above transformation method, there can be constructed *Yarrowia lipolytica* PHA1 containing pSUT-PHA1 and *Yarrowia lipolytica* PHA2 containing pSUT-PHA2.

As the host, *Candida maltosa* CHAL [S. Kawai et al., Agric. Biol. Chem., Vol. 55, 59–65 (1991)] can also be used. By transforming this strain with the polymer synthesis-associated gene expression cassette by the above transformation method, *Candida maltosa* CHAL containing pUTA-ORF23 can be constructed.

(5) Production of a Polyester

In the method of producing a polyester according to the present invention, the polyester is harvested from a culture obtained by growing the transformant of the invention.

The production of a polyester by cultivation of a transformant of the invention can be carried out in the following manner. The carbon source for use in this cultivation may be any substance that the yeast is able to assimilate. Furthermore, when the expression of the promoter is inductive, an inducer can be added as needed. There are cases in which the inducer serves as a principal source of carbon. Referring to nutrients other than the carbon source or sources, a medium containing sources of nitrogen, inorganic salts and other organic nutrient sources can be utilized. The cultivation temperature may be a temperature at which that strain can grow but is preferably 20° C. to 40° C. The cultivation time is not particularly restricted but may range from about 1 day to 7 days. Thereafter, the polyester can be harvested from the grown cells or the culture broth thus obtained.

The carbon source which can be used includes carbohydrates such as glucose, glycerol, sucrose, etc., oils and fats, fatty acids, and even n-paraffins and the like. As said oils and fats, there can be used rapeseed oil, coconut oil, palm oil and palm kernel oil, among others. As said fatty acids, there can be mentioned saturated or unsaturated fatty acids such as hexanoic acid, octanoic acid, decanoic acid, lauric acid, oleic acid, palmitic acid, linoleic acid, linolenic acid, myristic acid, etc., and derivatives of such fatty acids, e.g. their esters and salts. The cultivation of *Candida maltosa* or *Yarrowia lipolytica*, for instance, can be carried out using an oil or fat as the carbon source. In the case of a yeast which cannot assimilate oils and fats at all or cannot assimilate them with good efficiency, the efficiency can be improved by adding lipase to the medium. Moreover, by transforming the lipase gene, an oil-assimilating function can be imparted.

Moreover, by using a fatty acid or n-paraffin having an odd number of carbon atoms as the carbon source, the proportion of the odd-number component of the carbon chain can be increased in the copolyester of 3-hydroxyalkanoic acids of the above general formula (1).

The nitrogen source includes ammonia, ammonium salts such as ammonium chloride, ammonium sulfate, ammonium phosphate, etc., peptone, meat extract, yeast extract and so on. As to said inorganic salts, there can be mentioned, for example, potassium phosphate, potassium diphosphate, magnesium phosphate, magnesium sulfate and sodium chloride, etc.

As other nutrients, there can be mentioned, for example, amino acids, such as glycine, alanine, serine, threonine, proline, etc., and vitamins such as vitamin B1, vitamin B12, biotin, nicotinamide, pantothenic acid and vitamin C, etc.

In the practice of the invention, the following techniques can be used for harvesting the polyester from the grown cells. Thus, after completion of cultivation, the culture broth is centrifuged with centrifuge to separate the cells and those cells are washed with distilled water, methanol or the like and dried. From the dry cells, the polyester is extracted into an organic solvent such as chloroform. From this organic solvent solution containing the polyester, the cellular component is removed by filtration or the like and the polyester is precipitated by adding a poor solvent, such as methanol, hexane or the like, to the filtrate. After removal of the supernatant by filtration or centrifugation, the precipitated polyester is dried and recovered. The thus-obtained polyester is analyzed by gas chromatography or nuclear magnetic resonance spectrometry, for instance.

The method of producing a polyester according to the present invention, constituted as above, is capable of producing a copolyester of 3-hydroxyalkanoic acids of the above general formula (1) with good productivity.

Furthermore, by the above-mentioned method which comprises constructing a recombinant *Yarrowia lipolytica* strain containing the plasmid pSUT-PHA1 or pSUT-PHA2 or a recombinant *Candida maltosa* strain containing the plasmid pUTA-ORF23, for instance, and growing either strain, said copolyester P(3HB-co-3HH) resulting from the copolymerization of 3-hydroxybutyric acid of the above general formula (2) and 3-hydroxyhexanoic acid of the above general formula (3) can be produced.

EXAMPLES

The following examples illustrate the present invention in further detail. It should, however, be understood that the technical scope of the invention is by no means defined by those examples.

Example 1

Polyester Synthesis-associated Genes (a) When *Yarrowia lipolytica* was Used as the Host As polyester synthesis-associated enzyme gene, the PHA synthase gene (phac; SEQ ID NO:1) derived from *Aeromonas caviae* and (R)-specific enoyl-CoA hydratase gene (phaJ; SEQ ID NO:2) which converts enoyl-CoA, an intermediate in the β-oxidation pathway, to the monomeric (R)-3-hydroxyacyl-CoA [T. Fukui et al., FEMS Microbiology Letters, Vol. 170, 69–75 (1999)] were used.

(b) When *Candida maltosa* was Used as the Host

As polyester synthesis-associated enzyme gene, this gene was constructed with reference to the amino acid sequences of *Aeromonas caviae*-derived PHA synthase and (R)-specific enoyl-CoA hydratase which converts enoyl-CoA, an intermediate in the β-oxidation pathway, to the monomeric (R)-3-hydroxyacyl-CoA [T. Fukui et al., FEMS Microbiology Letters, Vol. 170, 69–75 (1999)].

*Candida maltosa* is a yeast which translates the CTG codon toserine, not to leucine. Therefore, for use in *Candida maltosa*, CTG was not assigned to the leucine-specifying codon. As the codon corresponding to each amino acid, the codon with the high frequency of usage in *Candida maltosa* was preferentially selected. For information on the frequency of usage of each codon, Klaus Wolf: Nonconventional Yeast in Biotechnology (published by Springer) was consulted. Specifically, ATG and TGG were assigned to the methionine-specifying codons and the tryphtophan-specifying codons, respectively. TTT or TTC was assigned alternately to the phenylalanine-specifying codons. As the leucine-specifying codons, CTC and CTG, both of which are used in DNA sequences of *Aeromonas caviae*, were modified to TTA and TTG respectively, while TTA and TTG were used as such. As the isoleucine-specifying codons, ATC and ATA, both of which are used in DNA sequences of *Aeromonas caviae*, were modified to ATT and ATC respectively, while ATT was used as such. As the valine-specifying codons, GTG and GTA, both of which are used in DNA sequences of *Aeromonas caviae*, were modified to GTT, while GTC and GTT were used as such. As the serine-specifying codons, AGC, TCA and TCG, all of which are used in DNA sequences of *Aeromonas caviae*, were modified to TCT, while TCC and TCT were used as such. As the proline-specifying codons, all of the corresponding codons were modified to CCA. As the threonine-specifying codons, ACC, ACG and ACA, all of which are used in DNA sequences of *Aeromonas caviae*, were modified to ACT, ACC and ACC respectively, while ATC was used as such. As the alanine-specifying codons, GCC, GCG and GCA, all of which are used in DNA sequences of *Aeromonas caviae*, were modified to GCT, GCC and GCT respectively, while GCT was used as such. As the tyrosine-specifying codons, TAT and TAC were assigned alternatively as the tyrosine-specifying codons as used in DNA sequences of *Aeromonas caviae*. As stop codons, TAA was used. As the histidine-specifying codons, CAT and CAC were assigned alternatively as the histidine-specifying codons as used in DNA sequences of *Aeromonas caviae*. As the glutamine-specifying codons, all of the corresponding codons were modified to CAA. AAT and AAC were assigned alternatively to the corresponding asparagine-specifying codons. As the lysine-specifying codons, all of the corresponding codons were modified to AAA. As the asparic acid-specifying codons, all of the corresponding codons were modified to GAT. As the glutamic acid-specifying codons, all of the corresponding codons were modified to GAA. As the cysteine-specifying codons, all of the corresponding codons were modified to TGT. As the arginine-specifying codons, all of the corresponding codons were modified to AGA. As the glycine-specifying codons, all of the corresponding codons were modified to GGT. In *Aeromonas caviae*-derived PHA synthase DNA sequence, two T nucleotides (at No. 969 and at No. 1449) were modified to C so as to construct two KpnI sites. Amino acid sequence structure was not changed by these substitutions.

Thus, PHA synthase gene (ORF2; SEQ ID NO:3) and (R)-specific enoyl-CoA hydratase gene (ORF3; SEQ ID NO:4) were accordingly designed, and based on these sequences, ORF2 and ORF3 were constructed by total synthesis.

Example 2

Construction of a Recombinant Plasmid and a Recombinant Strain (a) When *Yarrowia lipolytica* was Used as the Host In order that the above genes may be expressed in *Yarrowia lipolytica*, the *Yarrowia lipolytica* AlK3 gene promoter ALK3p (SEQ ID NO:5) (GenBank AB010390) was ligated upstream of the 5' end of each gene. The restriction enzyme sites necessary for linking the promoter to the structural gene were prepared by PCR. The primer sequences used in PCR are shown in SEQ ID NO:8 through NO:14. PCR was carried out in 25 cycles of 94° C.×1 min., 55° C.×2 min., 72° C.×3 min. for amplification of the particular gene fragment. The polymerase used was Takara Shuzo's ExTaq. Regarding the promoter region, ALK3X with XbaI at 5'-end and NdeI at 3'-end and ALK3S with SacII at 5'-end and NdeI at 3'-end were prepared from SEQ ID NO:8 and SEQ ID NO:9 or SEQ ID NO:9 and SEQ ID NO:10 respectively, using SEQ ID NO:5 as a template.

As regards phac, an about 100 bp-fragment with NdeI at 5'-end and PstI at 3'-end was prepared from SEQ ID NO:11 and SEQ ID NO:12 using SEQ ID NO:1 as a template. To this fragment was ligated the remaining PstI-BamHI fragment sized about 1700 bp to construct the full-length phac with NdeI at 5'-end and BamHI at 3'-end. As to phaJ, phaJ fragment with NdeI at 5'-end and KpnI at 3'-end was prepared from SEQ ID NO:13 and NO:14 using SEQ ID NO:2 as a template.

As to the vector, the plasmid pSUT5 (FIG. 1, SEQ ID NO:19) and the plasmid pSUT6 prepared by changing the NdeI site of pSUT5 to an XbaI site by using a linker DNA shown in SEQ ID NO:20 were used. To the multicloning site SacII, KpnI of the above pSUT6, ALK3S and phaJ were ligated to construct the plasmid pSUT-phaJ (FIG. 3). Further, ALK3X and phaC were ligated to the multicloning site XbaI, BamHT of pSUTS to construct a plasmid pSUT-PHA1 (FIG. 4).

Figure 10:
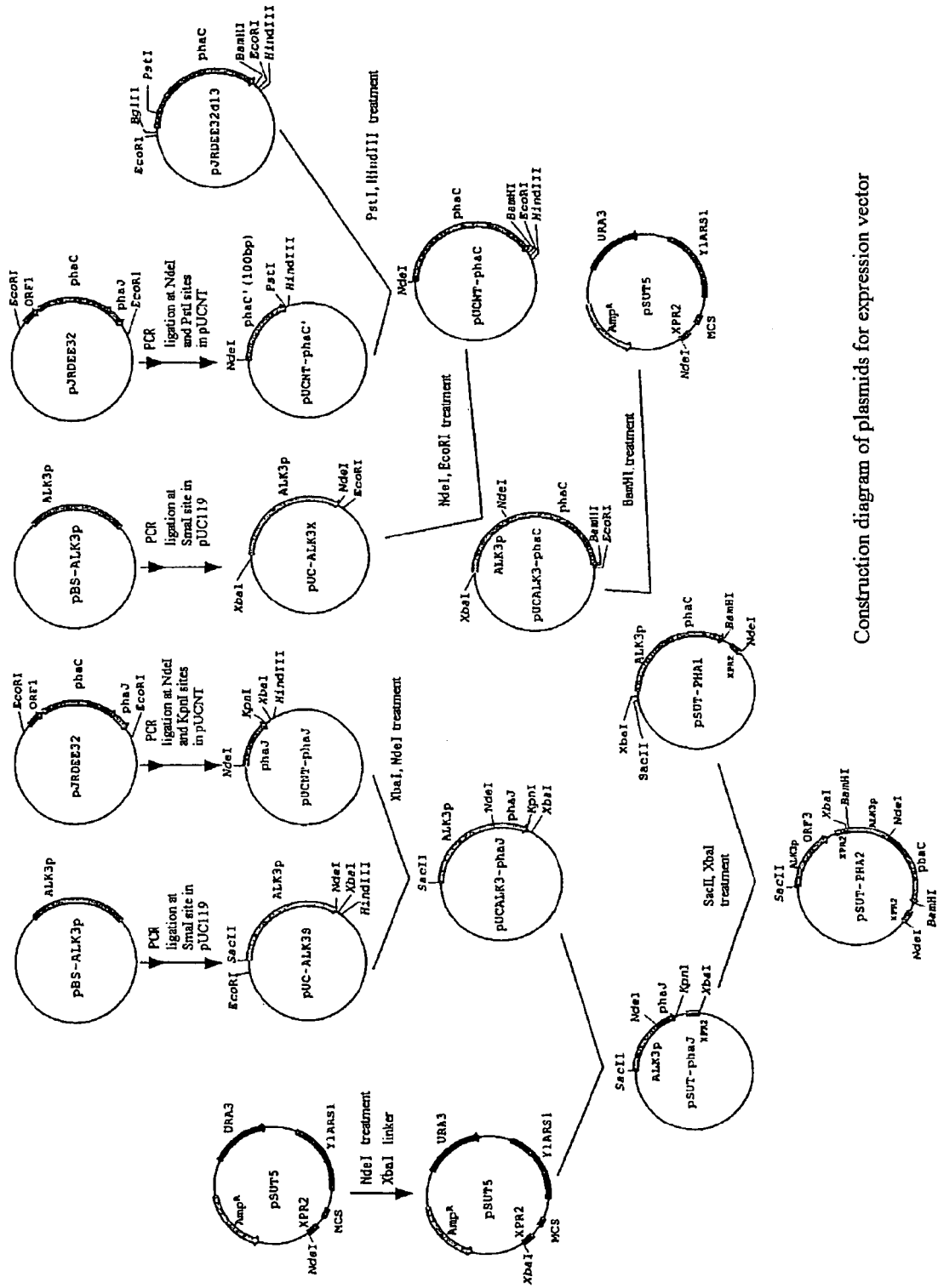
FIG. 10 is a plasmid construction diagram showing the procedure of constructing the plasmid according to Example 2 (a).

Then, from the plasmid pSUT-phaJ, ALK3S, phaJ and downstream terminator were excised as a unit using SacII and XbaI and ligated to the SacII, XbaI site of plasmid pSUT-PHA1 to construct a plasmid pSUT-PHA2 (FIG. 5). In this manner, two kinds of plasmids for recombination, pSUT-PHA1 and pSUT-PHA2, were constructed. By the above procedure, a gene expression cassette for producing a copolyester of 3-hydroxyalkanoic acids of the above general formula (1) in the yeast *Yarrowia lipolytica* was constructed. The overall construction diagram is shown in FIG. 10.

As the host, *Yarrowia lipolytica* CXAU1 strain (T. Iida et al., Yeast, 14, 1387–1397 (1998)) was used. For the introduction of the constructed plasmid into the host, Fast Track™-Yeast-Transformation Kit$^{SM}$ (Geno Technology) was used. Transformation was carried out in accordance with the protocol and using a selection plate (0.67 w/v % yeast nitrogen base without amino acid, 2 w/v % glucose, 24 mg/L adenine hydrochloride, 2 w/v % agar), a recombinant strain was obtained.

(b) When *Candida maltosa* was Used as the Host

In order that said ORF2 and ORF3 could be expressed in *Candida maltosa*, the *Candida maltosa* AlK1 gene promoter ALK1p (SEQ ID NO:6, GenBank D00481) was ligated upstream of the 5'-end of each gene and the *Candida maltosa* AlK1 gene terminator ALK1t (SEQ ID NO:7) was ligated downstream of the 3'-end. PCR was used for the preparation of the restriction enzyme sites necessary for ligating the promoter and terminator to the structural gene. The primer sequences used for PCR are shown in SEQ ID NO:15 through NO:18. The PCR was carried out in 25 cycles of 94° C.×1 min., 55° C.×2 min., 72° C.×3 min. for amplification of the particular gene fragment. The polymerase used was Takara Shuzo's ExTaq. As to the promoter region, ALK1p with PvuII at 5'-end and EcoRI at 3'-end was prepared from SEQ ID NO:15 and NO:16 using SEQ ID No:6 as a template. As to the terminator region, ALK1t with Hind III at 5'-end and EcoRV at 3'-end was prepared from SEQ ID NO:17 and NO:18 using SEQ ID NO:7 as a template. Finally, as the vectors to which ORF2 and ORF3 were to be ligated, there were used pUTU [M. Ohkuma et al., J. Biol. Chem., Vol. 273, 3948–3953 (1998)] which is obtained by ligating the autonomously replicating sequence (ARS) of *Candida maltosa* (GenBank D29758) and URA3 gene (GenBank D12720) to pUC19 and pUTA1 (FIG. 2) which is obtained by modifying the marker gene from Ura3 to Ade1 using *Candida maltosa* ADE1 gene (SEQ ID NO:21; GenBank D00855). pUTA1 was constructed by removing URA3 gene from pUTU1 with Xho1 and ligating the ADE1 gene fragment as excised with SalI.

Figure 6:
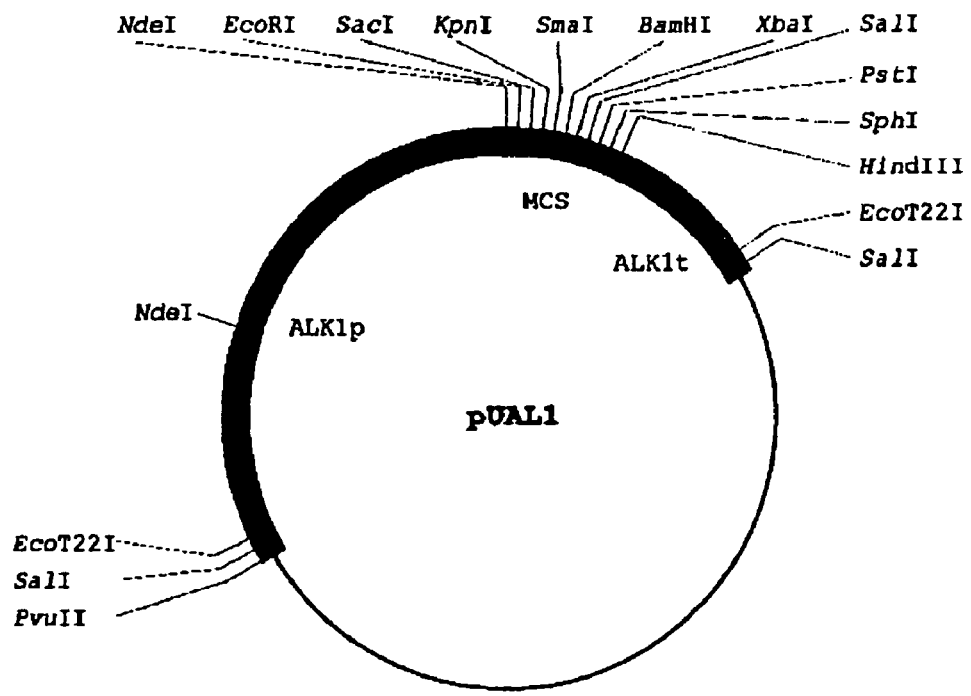
FIG. 6 is a schematic diagram showing the plasmid pUAL1 constructed in Example 2 (b).
Figure 7:
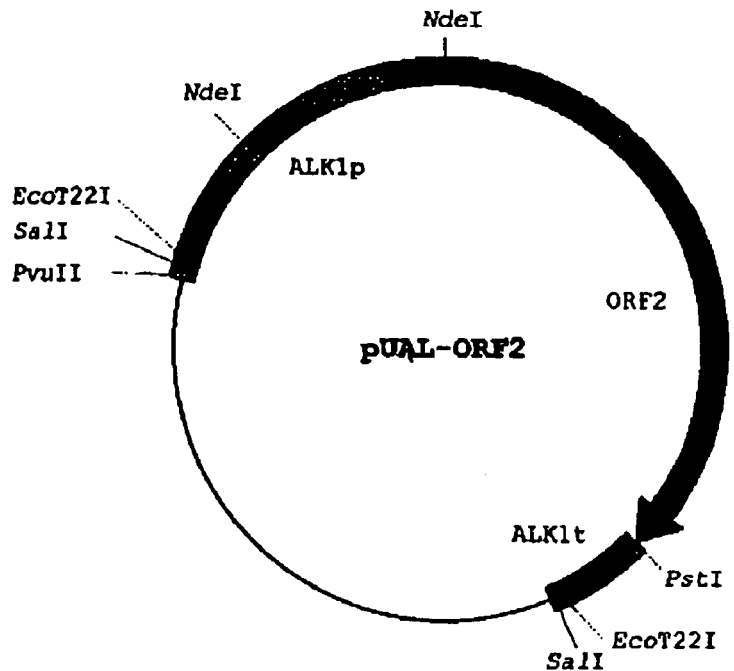
FIG. 7 is a schematic diagram showing the plasmid pUAL-ORF2 constructed in Example 2 (b).
Figure 8:
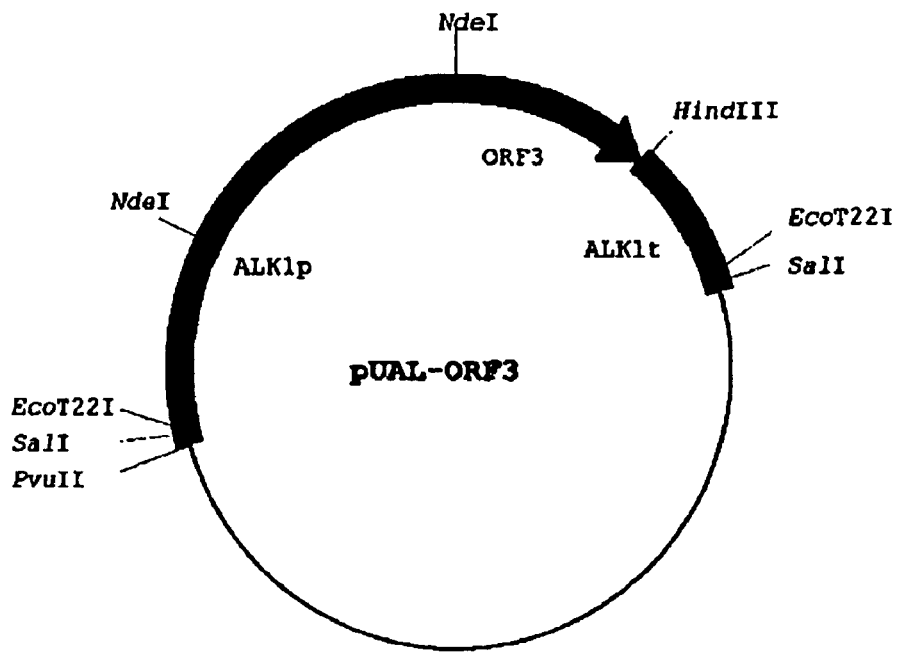
FIG. 8 is a schematic diagram showing the plasmid pUAL-ORF3 constructed in Example 2 (b).

ALK1p was ligated to the PvuII, EcoRI site of pUCNT (described in WO94/03613) and ALK1t was ligated to the HindIII, SspI site of the pUCNT to construct pUAL1 (FIG. 6). Then, ORF2 was ligated to the NdeI, PstI site of pUAL1 to construct a plasmid pUAL-ORF2 (FIG. 7). Moreover, in the course of construction of pUAL1, ORF3 was ligated to the NdeI, HindIII site of pUCNT-ALK1 and, further, ALK1p was ligated to construct pUAL-ORF3 (FIG. 8).

Figure 9:
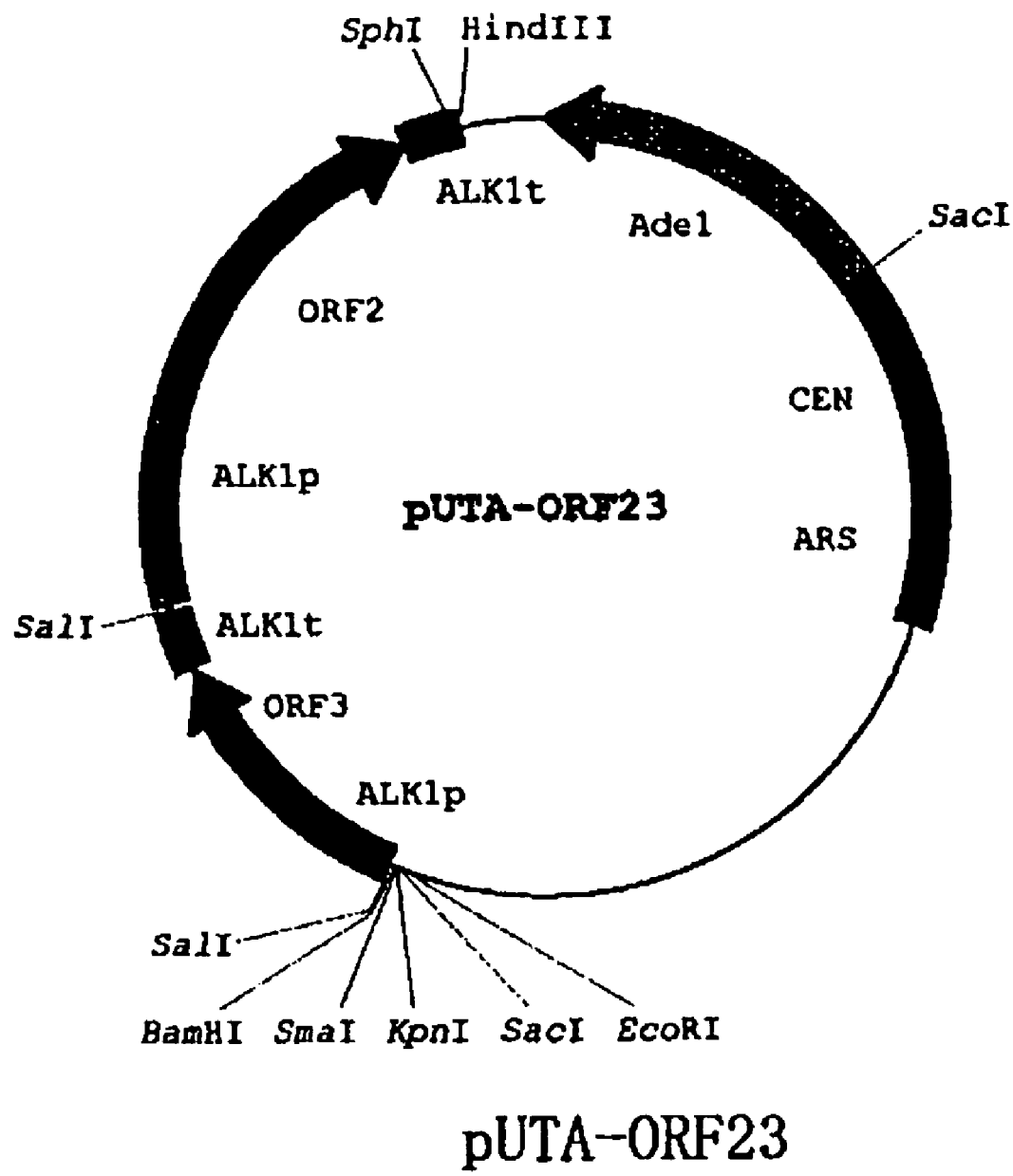
FIG. 9 is a schematic diagram showing the plasmid pUTA-ORF23 constructed in Example 2 (b).
Figure 11:
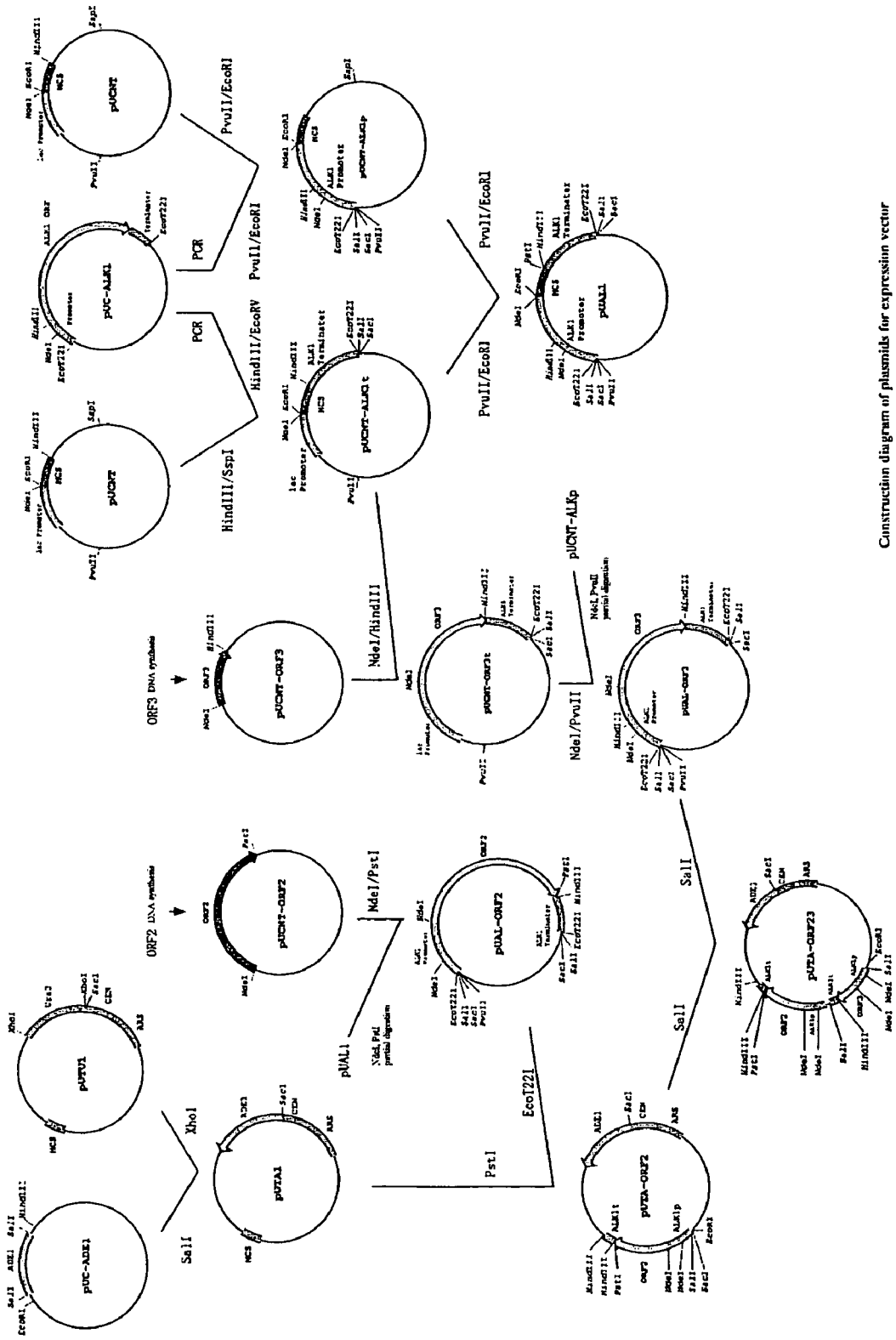
FIG. 11 is a plasmid construction diagram showing the procedure of constructing the plasmid according to Example 2 (b).

Then, the ORF2, upstream promoter and downstream terminator were excised as a unit from the plasmid pUAL-ORF2 using EcoT22I and ligated to the PstI site of pUTA1 to construct pUTA-ORF2. Furthermore, using SalI, ORF3, the upstream promoter and downstream terminator were excised as a unit from pUAL-ORF3 and ligated to the SalI site of pUTA-ORF2 to construct a plasmid pUTA-ORF23 (FIG. 9). By the above procedure, a gene expression cassette for producing a copolyester of 3-hydroxyalkanoic acids of the above general formula (1) was constructed in the yeast *Candida maltosa*. The overall construction diagram is shown in FIG. 11.

As the host, *Candida maltosa* CHA1 (S. Kawai et al., Agric. Biol. Chem., Vol. 55, 59–65 (1991)) was used. For introduction of the plasmid constructed into the host, Fast Track™-Yeast Transformation Kit$^{SM}$ (Geno Technology) was used. Transformation was carried out in accordance with the protocol and using a selection plate (0.67 w/v % yeast nitrogen base without amino acid, 2 w/v % glucose, 24 mg/L of histidine, 2 w/v % agar), a recombinant strain was obtained.

Example 3

Productioon of P(3HB-co-3HH) Using a Recombinant Strain of *Yarrowia lipolytica*

The recombinant strains of *Yarrowia lipolytica* containing the plasmids pSUT5, pSUT-PHA1 and pSUT-PHA2 were cultured in the following manner. As the preculture medium, YPD medium (1 w/v % yeast-extract, 2 w/v % Bacto-Pepton, 2 w/v % glucose) was used. As the polyester production medium, 1/4 YP medium (0.25 w/v % yeast extract, 0.5 w/v % Bacto-Pepton) and a mineral medium (0.7 w/v % $KH_2PO_4$, 1.3 w/v % $(NH_4)_2HPO_4$, 0.5 w/v % Pro-Ex AP-12 (Banshu Condiment), 0.04 w/v % adenine, 1 ppm thiamine hydrochloride, 1 v/v % trace metal salt solution (as dissolved in 0.1 N—HCl, 8 w/v % $MgSO_4.7H_2O$, 0.6 w/v % $ZnSO_4.7H_2O$, 0.9 w/v % $FeSO_4.7H_2O$, 0.05 w/v % $CuSO_4.5H_2O$, 0.1 w/v % $MnSO_4.6-7H_2O$, 1 w/v % NaCl)) supplemented with 2 w/v % palm oil was used.

A 500-ml Sakaguchi flask containing 100 ml of the preculture medium was inoculated with 100 µl of a glycerol stock of each recombinant strain and after 20 hours of culture, a 2-L Sakaguchi flask containing 500 mL of the production medium was inoculated with the preculture at the 1 v/v % level. The inoculated flask was incubated at the cultivation temperature of 30° C. and the shaking speed of 120 rpm. The cultivation time was 24 hours for the YPD medium and 72 hours for the mineral medium. After autoclaving, the culture broth was centrifuged to harvest cells, which were then washed with methanol and lyophilized. The dry cells were weighed.

The dry cells thus obtained were crushed and extracted with 100 ml of chloroform added under stirring overnight. The extract was filtered to remove cells and the filtrate was concentrated to 1 to 2 ml on an evaporator. To the concentrate was added 10 ml of hexane to precipitate the hexane-insoluble fraction.

Figure 12:
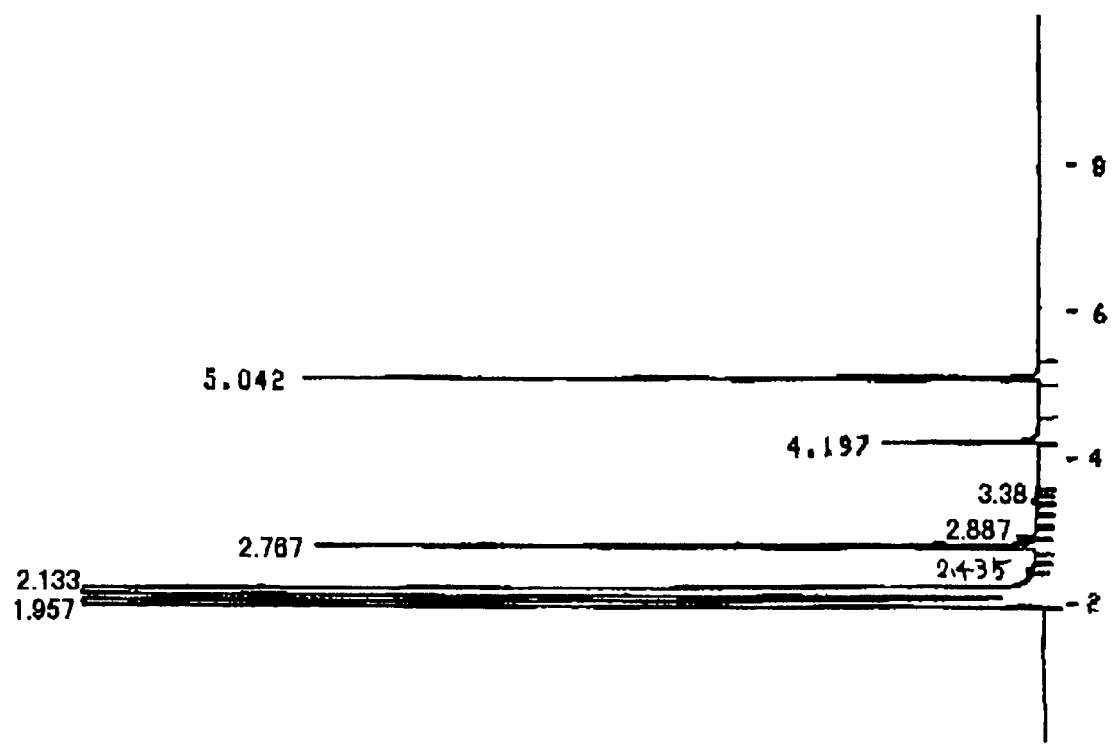
FIG. 12 shows the result of an analysis, by capillary gas chromatography, of the polyester produced in Example 3.
Figure 13:
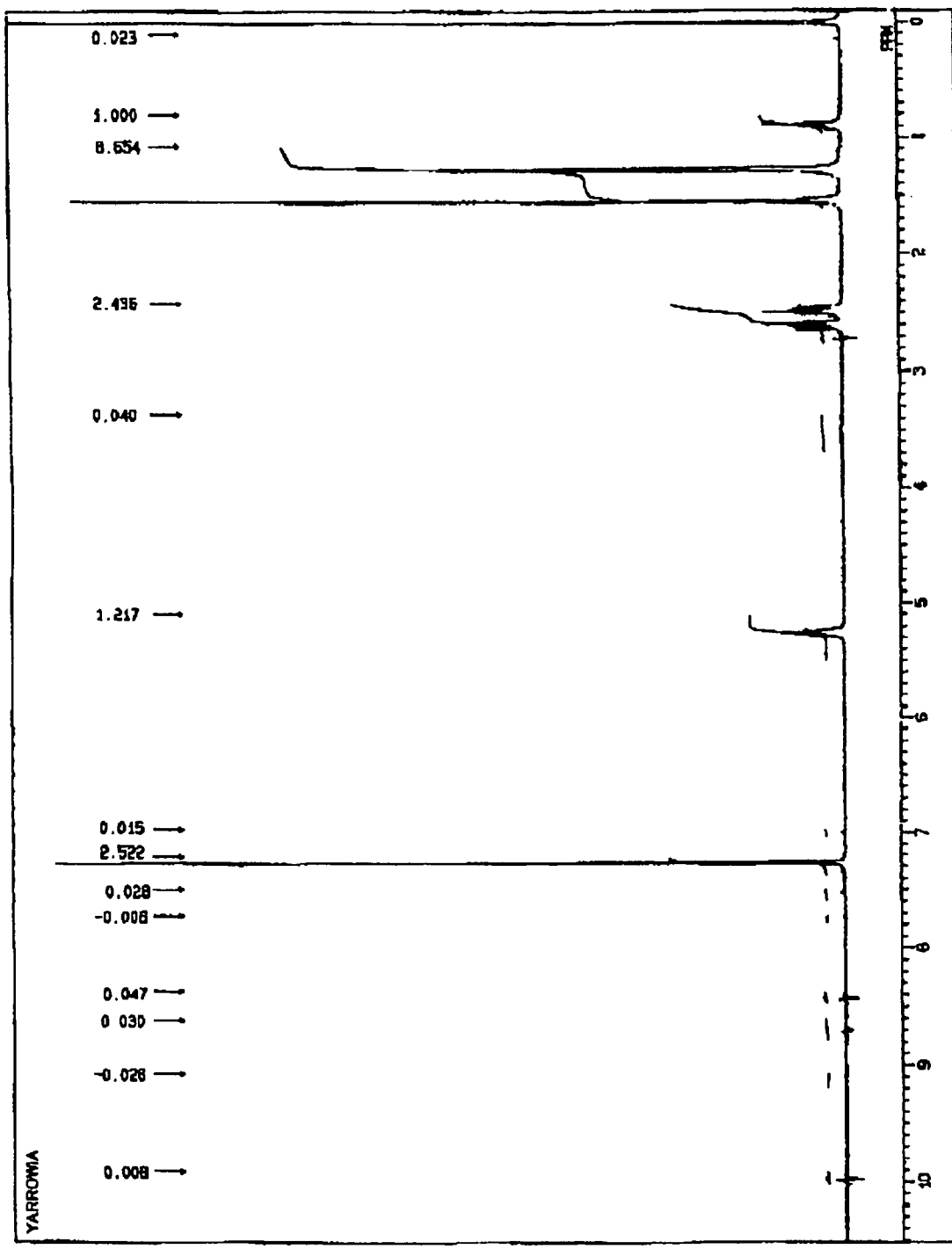
FIG. 13 is an NMR analysis chart of the polyester produced in Example 3.
Figure 14:
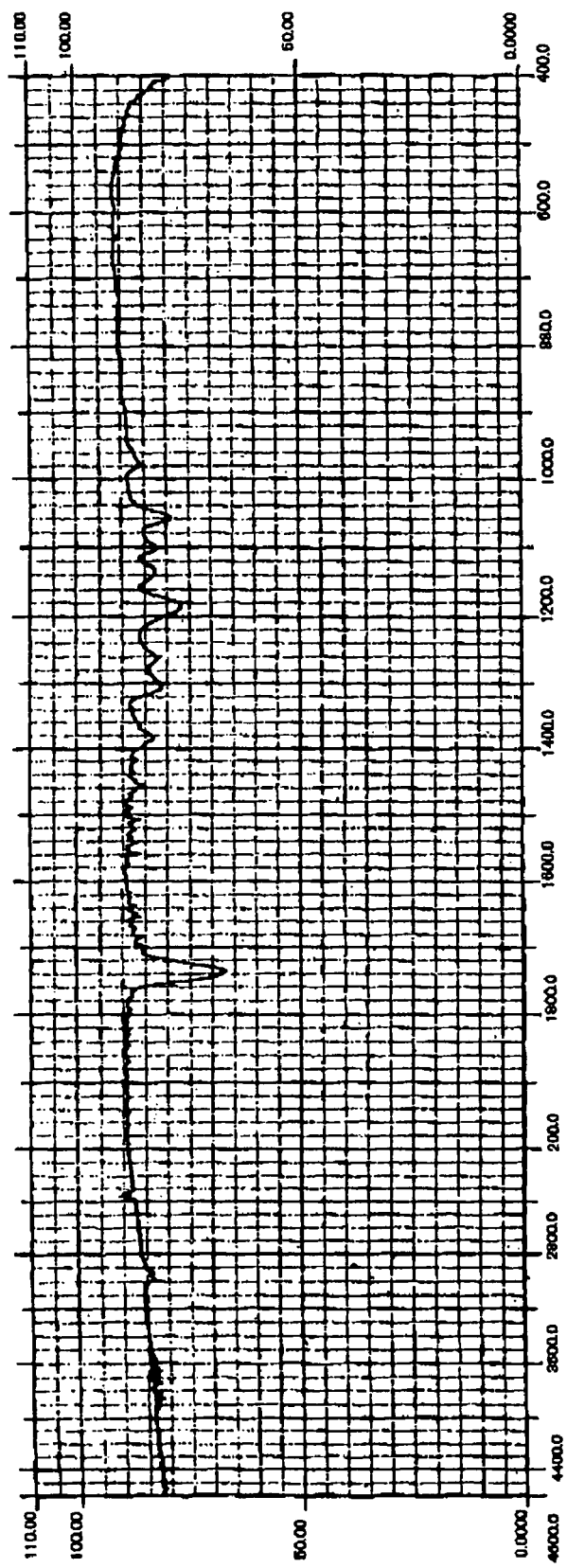
FIG. 14 is an IR analysis chart of the polyester produced in Example 3.

To about 2 mg of the hexane-insoluble fraction thus obtained were added 500 µl of sulfuric acid-methanol mixture (15:85) and 500 µl of chloroform and, after sealing, heated at 100° C. for 140 minutes to obtain the polyester decomposition product methyl ester. After cooling, 0.3 g of sodium hydrogen carbonate was added for neutralization. To this was added 1 ml of diisopropyl ether, and the mixture was stirred with a stirrer. This was followed by centrifuging and the organic solvent layer was separated and analyzed for composition by capillary gas chromatography. The gas chromatograph used was Shimadzu GC-17A and the capillary column used was GL Science's NEUTRA BOND-1 (column length 25 m, column in. dia. 0.25 mm, liquid film thickness 0.4 µm). As to temperature conditions, the temperature was increased from the initial level of 100° C. at the rate of 8° C./min. The obtained results of analysis are shown in Table 1 and the chart of a sample (3) is given in FIG. 12. The NMR analysis (JEOL, JNM-EX400) and IR analysis (Shimadzu Corporation, DR-800) of the hexane-insoluble fraction obtained were also carried out. As an example, the result on a sample (6) are shown in FIGS. 13 and 14, respectively.

TABLE 1

Culture and analysis result

| Sample | Medium | Strain | Weight of cells (g/L) | Amount of polymer accumulated (wt %) | 3HH Composition (mol %) |
|---|---|---|---|---|---|
| (1) | 1/4 YP | Control | 3.56 | $8.9 \times 10^{-2}$ | |
| (2) | | PHA1 | 3.65 | $1.9 \times 10^{-1}$ | |
| (3) | | PHA2 | 3.43 | $2.6 \times 10^{-1}$ | 15 (GC) |
| (4) | Mineral | Control | 0.15 | $6.7 \times 10^{-2}$ | |
| (5) | | PHA1 | 0.19 | $1.4 \times 10^{-1}$ | |
| (6) | | PHA2 | 0.17 | 1.8 | 27 (NMR) |

It is apparent from the above results that the copolyester P (3HB-co-3HH) can be produced by means of the yeast *Yarrowia lipolytica*.

It was also found that the polymer occurred, though in a small amount, in the yeast, too.

Example 4

Production of P(3HB-co-3HH) with a Recombinant Strain of *Candida maltosa*

The recombinant strain of *Candida maltosa* containing the plasmid pUTA1 or pUTA-ORF23 was cultured in the following manner. As the preculture medium, YNB medium (0.67 w/v % yeast nitrogen base without amino acid) supplemented with 1 w/v % casamino acids and 2 w/v % palm oil was used. As the polyester production medium, YNB medium supplemented with 1 w/v % casamino acids and containing, as a source of carbon, ① 2 w/v % palm oil, ② w/v % coconut oil, ③ 2 w/v % tetradecane or ④ 2 w/v % hexadecane.

A 500-ml Sakaguchi flask containing 50 ml of the preculture medium was inoculated with 100 μl of a glycerol stock of each strain and incubated for 20 hours. Then, a 2-L Sakaguchi flask containing 500 mL of the production medium was inoculated with the above preculture at the 10 v/v % level. Culture was carried out at the cultivation temperature of 30° C. and the shaking speed of 120 rpm for the cultivation time of 72 hours. The resulting culture broth was autoclaved and centrifuged to harvest cells and the cells thus obtained were washed with methanol and lyophilized. The dry cells were weighed.

The dry cells thus obtained were crushed and extracted with 100 ml of chloroform added under stirring overnight. The extract was filtered to remove cells and the filtrate was concentrated to 1 to 2 ml on an evaporator. To the concentrate was added 10 ml of hexane to precipitate the hexane-insoluble fraction.

Figure 15:
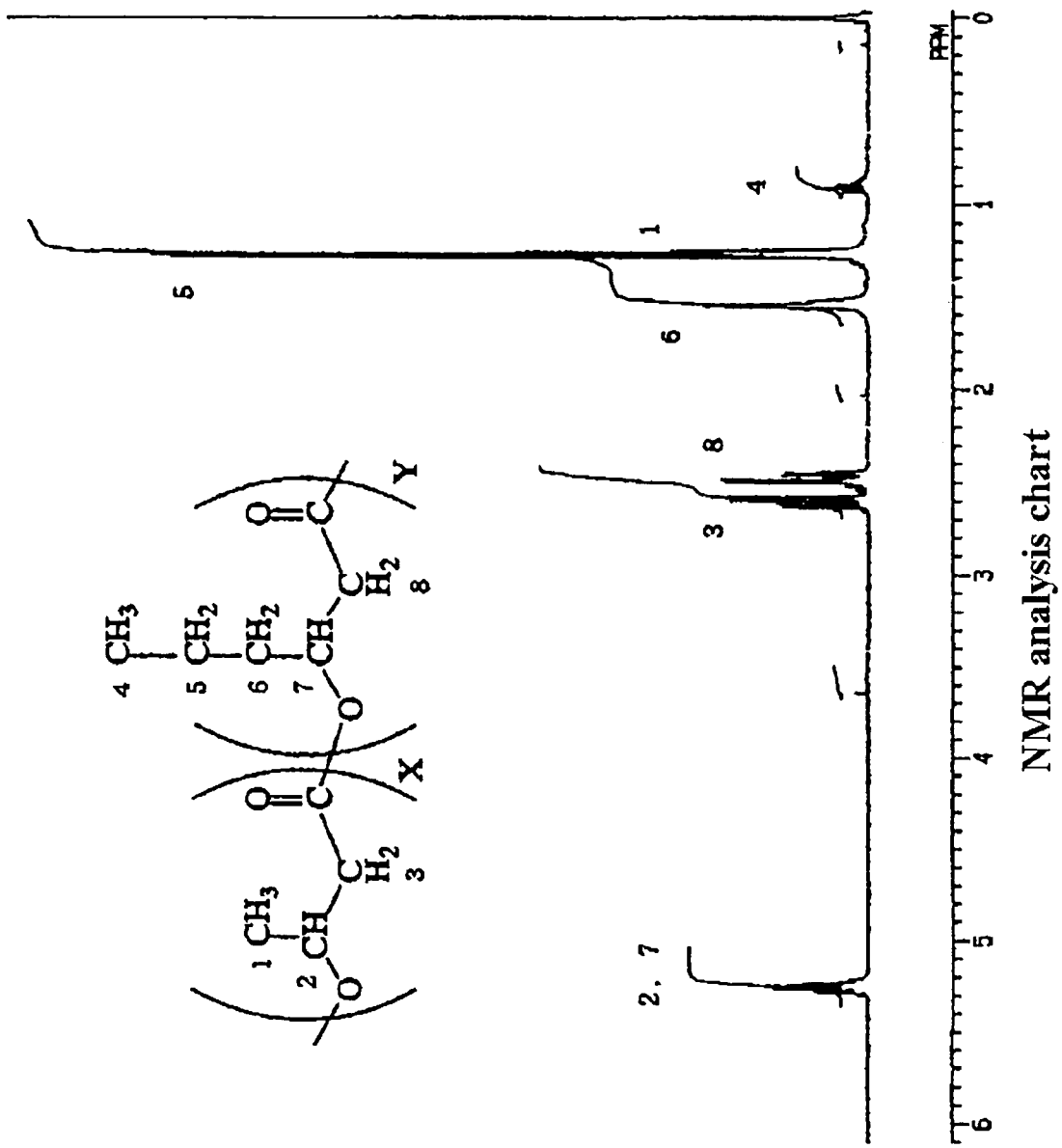
FIG. 15 is an NMR analysis chart of the polyester produced in Example 4.

As a result, white precipitates were found in cultures of the plasmid pUTA-ORF23-containing recombinant strain as cultured using coconut oil, tetradecane and hexadecane (Table 2). The results of NMR analysis (JEOL, JNM-EX400) of the hexane-insoluble fraction obtained in the culture using coconut oil are shown in Table 2 and FIG. 15.

TABLE 2

Culture of a recombinant strain

| Carbon source | Weight of cells (g/L) | Polymer accumulated |
|---|---|---|
| Palm oil | 12.5 | – |
| Coconut oil | 10.3 | ++ |
| Tetradecane | 4.4 | + |
| Hexadecane | 3.6 | + |

It is apparent from the above results that the copolyester P(3HB-co-3HH) can be produced by means of the yeast *Candida maltosa*.

INDUSTRIAL APPLICABILITY

In accordance with the present invention, a copolyester of 3-hydroxyalkanoic acids of the above general formula (1), which is biodegradable and has good physical properties, can be produced by using a yeast.

---

The invention claimed is:

1. A transformant
wherein at least one gene expression cassette, comprising a polyester synthesis-associated enzyme gene, a promoter and a terminator, has been introduced into a yeast which belongs to any of the genera *Candida, Hansenula, Kluyveromyces, Phaffia, Pichia, Schizosaccharomyces, Schwanniomyces, Trichosporon,* and *Yarrowia,* and
wherein the promoter is isolated from *Yarrowia lipolytica* ALK3 gene encoding an n-alkane-inducible cytochrome P450.

2. A transformant
wherein at least one gene expression cassette, comprising a polyester synthesis-associated enzyme gene, a promoter and a terminator, has been introduced into a yeast which belongs to any of the genera *Candida, Hansenula, Kinyveromyces, Phaffia, Pichia, Schizosaceharomyces, Schwanniomyces, Trichosporon,* and *Yarrowia,* and
wherein the promoter is isolated from *Candida maltosa* ALK1 gene encoding an n-alkane-inducible cytochrome P450.

3. A transformant
wherein at least one gene expression cassette, comprising a polyester synthesis-associated enzyme gene, a promoter and a terminator, has been introduced into a yeast which belongs to any of the genera *Candida, Hansenula, Kluyveromyces, Phaffia, Pichia, Schizosaccharomyces, Schwanniomyces, Trichosporon,* and *Yarrowia,* and
wherein the terminator is isolated from *Candida maltosa* ALK1 gene encoding an n-alkane-inducible cytochrome P450.

4. An isolated polyester synthesis-associated enzyme gene wherein at least one codon CTG is replaced with codon TTA, TTG, CTT, CTC or CTA, and said gene expresses a functional polyester synthesis-associated enzyme in a yeast which translates codon CTG into serine.

5. The polyester synthesis-associated enzyme gene according to claim 4 which codes for an enzyme isolated from a bacterium.

6. The polyester synthesis-associated enzyme gene according to claim 5 wherein said bacterium is *Aeromonas caviae*.

7. The polyester synthesis-associated enzyme gene according to claim 6 wherein the enzyme gene isolated from *Aeromonas caviae* is a polyhydroxyalkanoate synthase gene or a (R)-specific enoyl-CoA hydratase gene.

8. The polyester synthesis-associated enzyme gene according to claim 7 wherein said polyhydroxyalkanoate synthase gene has the sequence represented by SEQ ID NO:3.

9. The polyester synthesis-associated enzyme gene according to claim 7 wherein said (R)-specific enoyl-CoA hydratase gene has the sequence represented by SEQ ID NO:4.

10. A transformant wherein at least one gene expression cassette has been introduced into a yeast, and said gene expression cassette comprises the polyester synthesis-associated enzyme gene according to claim 4.

11. A method of producing a polyester using the transformant according to claim 10, which comprises growing said transformant and harvesting a polyester from the resulting culture.

* * * * *

UNITED STATES PATENT AND TRADEMARK OFFICE
CERTIFICATE OF CORRECTION

PATENT NO. : 7,083,972 B2
APPLICATION NO. : 10/019543
DATED : August 1, 2006
INVENTOR(S) : Yokomizo et al.

It is certified that error appears in the above-identified patent and that said Letters Patent is hereby corrected as shown below:

| Column | Line |  |
|---|---|---|
| 9 | 25 | Change "CHAL" to --CHA1--. |
| 9 | 29 | Change "CHAL" to --CHA1--. |
| 10 | 57 | Change "phac" to --phaC--. |
| 12 | 22 | Change "phac" to --phaC--. |
| 12 | 26 | Change "phac" to --phaC--. |
| 33 | 65 | Change "*Kinyveromyces*" to --*Kluyveromyces*--. |
| 33 | 66 | Change "*Schizosaceharomyces*" to --*Schizosaccharomyces*--. |

Signed and Sealed this

Fifth Day of December, 2006

JON W. DUDAS
*Director of the United States Patent and Trademark Office*